(12) United States Patent
Miller et al.

(10) Patent No.: US 9,688,654 B2
(45) Date of Patent: Jun. 27, 2017

(54) COMPOUNDS INHIBITING LEUCINE-RICH REPEAT KINASE ENZYME ACTIVITY

(71) Applicant: Merck Sharp & Dohme Corp., Rahway, NJ (US)

(72) Inventors: Michael Miller, Scotch Plains, NJ (US); Kallol Basu, Hillsborough, NJ (US); Duane DeMong, Somerset, NJ (US); Jack Scott, Scotch Plains, NJ (US); Hong Liu, Hillsborough, NJ (US); Xing Dai, Cranford, NJ (US); Andrew Stamford, Chatham, NJ (US); Marc Poirier, Stewartsville, NJ (US); Paul Tempest, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/772,525

(22) PCT Filed: Feb. 27, 2014

(86) PCT No.: PCT/US2014/018895
§ 371 (c)(1),
(2) Date: Sep. 3, 2015

(87) PCT Pub. No.: WO2014/137725
PCT Pub. Date: Sep. 12, 2014

(65) Prior Publication Data
US 2016/0009681 A1    Jan. 14, 2016

(30) Foreign Application Priority Data

Mar. 4, 2013    (WO) ................ PCT/CN2013/072134

(51) Int. Cl.
| | | |
|---|---|---|
| *C07D 401/04* | (2006.01) | |
| *C07D 401/12* | (2006.01) | |
| *C07D 401/14* | (2006.01) | |
| *C07D 405/14* | (2006.01) | |
| *C07D 413/14* | (2006.01) | |
| *C07D 417/14* | (2006.01) | |
| *C07D 487/04* | (2006.01) | |
| *C07D 491/08* | (2006.01) | |
| *C07D 495/08* | (2006.01) | |
| *C07D 498/04* | (2006.01) | |
| *C07D 498/08* | (2006.01) | |

(52) U.S. Cl.
CPC ......... *C07D 401/04* (2013.01); *C07D 401/12* (2013.01); *C07D 401/14* (2013.01); *C07D 405/14* (2013.01); *C07D 413/14* (2013.01); *C07D 417/14* (2013.01); *C07D 487/04* (2013.01); *C07D 491/08* (2013.01); *C07D 495/08* (2013.01); *C07D 498/04* (2013.01); *C07D 498/08* (2013.01)

(58) Field of Classification Search
CPC .. C07D 401/04; C07D 401/12; C07D 401/14; C07D 405/14; C07D 413/14; C07D 417/14; C07D 487/04; C07D 491/08; C07D 495/08; C07D 498/04; C07D 498/08
See application file for complete search history.

(56) References Cited

U.S. PATENT DOCUMENTS

| | | |
|---|---|---|
| 7,776,890 B2 | 8/2010 | Oinuma et al. |
| 2004/0127536 A1 | 7/2004 | Bhagwat et al. |
| 2006/0079564 A1 | 4/2006 | Jansen et al. |
| 2009/0203690 A1 | 8/2009 | Akritopoulou-Zanze et al. |
| 2009/0221602 A1 | 9/2009 | Charrier et al. |
| 2012/0329780 A1 | 12/2012 | Thormann et al. |

FOREIGN PATENT DOCUMENTS

| | | |
|---|---|---|
| EP | 1380576 B1 | 1/2004 |
| EP | 1510516 | 3/2005 |
| WO | 0153268 A2 | 7/2001 |
| WO | 0210137 | 2/2002 |
| WO | 02083648 | 10/2002 |
| WO | 03035005 | 5/2003 |
| WO | 2006081230 | 8/2006 |
| WO | 2008068171 | 6/2008 |
| WO | 2008137105 | 11/2008 |
| WO | 2008154241 | 12/2008 |
| WO | 2009054984 | 4/2009 |
| WO | 2010017046 A1 | 2/2010 |
| WO | 2010083145 A1 | 7/2010 |
| WO | 2011141756 | 11/2011 |
| WO | 2012038743 | 3/2012 |
| WO | 2012058193 | 5/2012 |
| WO | 2012078777 | 6/2012 |
| WO | 2014137719 A1 | 9/2014 |
| WO | 2014137723 A1 | 9/2014 |
| WO | 2014137725 A1 | 9/2014 |
| WO | 2014137728 | 9/2014 |
| WO | 2015026683 A1 | 2/2015 |
| WO | 2015073344 A1 | 5/2015 |
| WO | 2016036586 A1 | 3/2016 |

*Primary Examiner* — Rebecca Anderson
(74) *Attorney, Agent, or Firm* — Keith D. MacMillan; John C. Todaro

(57) ABSTRACT

The present invention is directed to indazole compounds which are potent inhibitors of LRRK2 kinase and useful in the treatment or prevention of diseases in which the LRRK2 kinase is involved, such as Parkinson's Disease. The invention is also directed to pharmaceutical compositions comprising these compounds and the use of these compounds and compositions in the prevention or treatment of such diseases in which LRRK2 kinase is involved.

10 Claims, No Drawings

COMPOUNDS INHIBITING LEUCINE-RICH REPEAT KINASE ENZYME ACTIVITY

CROSS-REFERENCE TO RELATED APPLICATIONS

This Application is a U.S. National Stage Application under 35 U.S.C. 371 of PCT Application No. PCT/US2014/018895, Feb. 27, 2014, which claims priority under 35 U.S.C. 119(e) to PCT/CN2013/072134, filed Mar. 4, 2013.

BACKGROUND OF THE INVENTION

Parkinson's disease (PD) is a common neurodegenerative disease caused by progressive loss of mid-brain dopaminergic neurons leading to abnormal motor symptoms such as bradykinesia, rigidity and resting tremor. Many PD patients also experience a variety of non-motor symptoms including cognitive dysfunction, autonomic dysfunction, emotional changes and sleep disruption. The combined motor and non-motor symptoms of Parkinson's disease severely impact patient quality of life.

While the majority of PD cases are idiopathic, there are several genetic determinants such as mutations in SNCA, Parkin, PINK1, DJ-1 and LRRK2. Linkage analysis studies have demonstrated that multiple missense mutations in the Leucine-Rich Repeat Kinase 2 (LRRK2) gene lead to an autosomal late onset form of PD. LRRK2 is a 286 kDa cytoplasmic protein containing kinase and GTPase domains as well as multiple protein-protein interaction domains. See for example, Aasly et al., Annals of Neurology, Vol. 57(5), May 2005, pp. 762-765; Adams et al., Brain, Vol. 128, 2005, pp. 2777-85; Gilks et al., Lancet, Vol. 365, Jan. 29, 2005, pp. 415-416, Nichols et al., Lancet, Vol. 365, Jan. 29, 2005, pp. 410-412, and U. Kumari and E. Tan, FEBS journal 276 (2009) pp. 6455-6463.

In vitro biochemical studies have demonstrated that LRRK2 proteins harboring the PD associated proteins generally confer increased kinase activity and decreased GTP hydrolysis compared to the wild type protein (Guo et al., Experimental Cell Research, Vol, 313, 2007, pp. 3658-3670) thereby suggesting that small molecule LRRK2 kinase inhibitors may be able to block aberrant LRRK2-dependent signaling in PD. In support of this notion, it has been reported that inhibitors of LRRK2 are protective in models of PD (Lee et al., Nature Medicine, Vol 16, 2010, pp. 998-1000).

LRRK2 protein has also been demonstrated to be associated with Lewy bodies, a pathological hallmark of PD as well as other neurodegenerative diseases such as Lewy body dementia (Zhu et al., Molecular Neurodegeneration, Vol 30, 2006, pp. 1-17) thereby suggesting that LRRK2 may be associated with the pathogenesis of these diseases.

A growing body of evidence also suggests a role for LRRK2 in immune cell function in the brain with LRRK2 inhibition demonstrated to attenuate microglial inflammatory responses (Moehle et al., The Journal of Neuroscience Vol 32, 2012, pp. 1602-1611). Neuroinflammation is a hallmark of a number of neurodegenerative diseases such as PD and Alzheimer's disease, thereby suggesting that LRRK2 inhibitors may have utility in the treatment of neuroinflammation in these disorders.

Genome-wide association studies also highlight LRRK2 in the modification of susceptibility to the chronic autoimmune Crohn's disease and leprosy (Zhang et al., The New England Journal of Medicine, Vol 361, 2009, pp. 2609-2618; Umeno et al., Inflammatory Bowel Disease Vol 17, 2011, pp. 2407-2415). LRRK2 is also associated with certain types of cancer, e.g. melanoma as well as renal and thyroid carcinomas (Saunders-Pullman et al., Movement Disorders, Vol 25, 2010, pp. 2536-2541; Looyenga, et al., Proceedings of the National Academy of Sciences, USA, Vol 108, 2011, pp. 1439-1444).

Accordingly, compounds and compositions effective at modulating LRRK2 activity may provide a treatment for neurodegenerative diseases such as Parkinson's disease, Lewy body dementia, neuroinflammation, and for disease such as Crohn's disease, leprosy and cancer.

SUMMARY OF THE INVENTION

The present invention is directed to indazole compounds which are potent inhibitors of LRRK2 kinase and may be useful in the treatment or prevention of diseases in which the LRRK2 kinase is involved, such as Parkinson's Disease. The invention is also directed to pharmaceutical compositions comprising these compounds and the use of these compounds and compositions in the prevention or treatment of such diseases in which LRRK2 kinase is involved.

DETAILED DESCRIPTION OF THE INVENTION

The present invention is directed to compounds of Formula I:

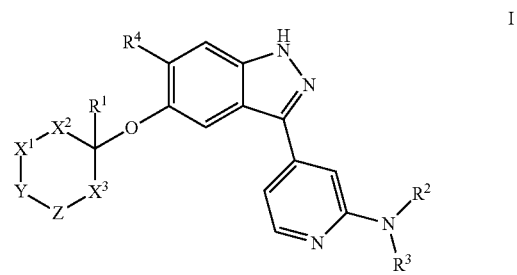

or a pharmaceutically acceptable salt thereof, wherein:
$X^1$, $X^2$ and $X^3$ are each independently selected from the group consisting of a bond or $CR^eR^f$;
Y is O, $CR^aR^b$ or $NR^c$;
Z is O, $CR^aR^b$ or $NR^c$;
$R^1$ is selected from the group consisting of hydrogen and $C_{1-6}$ alkyl, which is optionally substituted with one to three substitutents independently selected from the group consisting of halo, cyano, hydroxyl, $NR^cR^d$, $OR^5$ and $(C=O)OR^5$;
$R^2$ is selected from the group consisting of hydrogen and $C_{1-6}$ alkyl, which is optionally substituted with one to three substitutents independently selected from the group consisting of:
  a) halo,
  b) cyano,
  c) $R^5$,
  d) $R^7$,
  e) $OR^5$, and
  f) $NR^cR^d$;
$R^3$ is selected from the group consisting of:
  a) hydrogen,
  b) $C_{1-6}$ alkyl, which is optionally substituted with one to three substitutents independently selected from the group consisting of halo, cyano, $OR^5$ and $NR^cR^d$, c) cycloalkyl, which is optionally substituted with one to three substitutents independently selected from the group consisting of halo, cyano, $OR^5$ and $NR^cR^d$, d) heterocyclyl, which is optionally substituted with one to three substitutents independently selected from the group consisting of halo, cyano, oxo, $R^5$, $OR^5$ and $NR^cR^d$, e) heteroaryl, which is optionally substituted with one to three substitutents independently selected from the group consisting of halo, cyano, oxo, $R^5$, $OR^5$ and $NR^cR^d$;

f) $C_{4-8}$ cycloalkenyl, which is optionally substituted with one to three substitutents independently selected from the group consisting of halo, cyano, $OR^5$ and $NR^cR^d$, g) $(C=O)R^7$,
h) $(C=O)R^5$,
i) $S(O)_mR^5$, and
j) $S(O)_mR^7$;

or $R^2$ and $R^3$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:

a) halo,
b) oxo,
c) cyano,
d) $OR^5$,
e) $NR^cR^d$,
f) $SO_3H$,
g) $S(O)_mR^5$,
h) $S(O)_mR^7$
i) $R^5$,
j) $R^6$,
k) $R^7$,
l) $(C=O)R^5$,
m) $(C=O)OR^5$,
n) $(C=O)R^7$, and
o) $(C=O)NR^cR^d$;

$R^4$ is selected from the group consisting of hydrogen, halo, cyano, $OR^5$, aryl, heteroaryl, $C_{3-8}$ cycloalkyl, $C_{4-8}$ cycloalkenyl, $C_{4-8}$ heterocyclyl and $C_{1-6}$ alkyl, which is optionally substituted with one to three substitutents independently selected from the group consisting of halo, cyano, $OC_{1-3}$ alkyl, $NR^cR^d$ and hydroxyl;

$R^5$ is selected from the group consisting of hydrogen and $C_{1-6}$ alkyl, which is optionally substituted with one to three substituents independently selected from the group consisting of:

a) halo,
b) hydroxyl,
c) $OC_{1-6}$ alkyl,
d) $NR^cR^d$,
e) $(C=O)NR^cR^d$,
f) $S(O)_m$,
g) $S(O)_mR^8$,
h) $S(O)_mR^7$,
i) $R^7$ and
j) $OR^7$;

$R^6$ is $C_{1-6}$ alkyl, which is optionally substituted with one to three substituents independently selected from the group consisting of halo and hydroxyl;

or $R^5$ and $R^6$ can be taken together with the atoms to which they are attached to form a 4 to 6 membered heterocyclic, 3 to 8 membered carbocyclic, aryl or heteroaryl ring, wherein said heterocyclic and heteroaryl rings may contain from one to three heteroatoms selected from N, O and S, wherein said heterocyclic, carbocyclic, aryl and heteroaryl rings are optionally substituted with one to three substituents independently selected from the group consisting of:

a) halo,
b) oxo,
c) cyano,
d) hydroxyl,
e) $C_{1-3}$ alkyl, which is optionally substituted with one to three halo,
f) $C_{3-8}$ cycloalkyl,
g) $OC_{1-3}$ alkyl, which is optionally substituted with one to three halo, and
h) $OC_{3-8}$ cycloalkyl;

$R^7$ is selected from the group consisting of $C_{4-8}$ heterocyclyl, $C_{3-8}$ cycloalkyl, $C_{4-8}$ cycloalkenyl, aryl or heteroaryl, wherein said heterocyclyl, cycloalkyl, cycloalkenyl, aryl and heteroaryl groups are optionally substituted with one to three substituents independently selected from the group consisting of:

a) halo,
b) cyano,
c) hydroxyl,
d) oxo,
e) $C_{1-3}$ alkyl, which is optionally substituted with one to four substituents independently selected from the group consisting of hydroxyl, halo, cyano, heterocyclyl, $OC_{1-3}$ alkyl and $NR^cR^d$,
f) $OC_{1-3}$ alkyl, which is optionally substituted with one to four substituents independently selected from the group consisting of hydroxyl, halo, cyano, heterocyclyl, $OC_{1-3}$ alkyl $NR^cR^d$ and aryl,
g) $C_{3-8}$ cycloalkyl, which is optionally substituted with one to four substituents independently selected from the group consisting of hydroxyl, halo, cyano, heterocyclyl, $OC_{1-3}$ alkyl and $NR^cR^d$,
h) aryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$,
i) heteroaryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$,
j) heterocyclyl, which is optionally substituted with one to four substituents independently selected from the group consisting of hydroxyl, halo, cyano, $OC_{1-3}$ alkyl and $NR^cR^d$,
k) $C_{4-8}$ cycloalkenyl, which is optionally substituted with one to four substituents independently selected from the group consisting of hydroxyl, halo, cyano, heterocyclyl, $(OC_{1-3}$ alkyl and $NR^cR^d$;

$R^8$ is hydrogen or $C_{1-6}$ alkyl, which is optionally substituted with one to three substituents independently selected from the group consisting of:

a) halo,
b) cyano,
c) hydroxyl,
d) $OC_{1-3}$ alkyl, which is optionally substituted with one to four substituents independently selected from the group consisting of hydroxyl, halo and $NR^cR^d$, and
e) $C_{3-8}$ cycloalkyl;

$R^a$ is selected from the group consisting of hydrogen and $C_{1-6}$ alkyl;

$R^b$ is selected from the group consisting of hydrogen and $C_{1-6}$ alkyl;

$R^c$ is selected from the group consisting of:
  a) hydrogen and
  b) $C_{1-3}$ alkyl, which is optionally substituted with one to three substituents independently selected from the group consisting of halo, hydroxyl, cyano, heteroaryl, aryl, $NH(C_{1-3}$ alkyl), $N(C_{1-3}$ alkyl)$_2$, $OC_{1-6}$ alkyl, and $C_{3-8}$ cycloalkyl;

$R^d$ is selected from the group consisting of:
  a) hydrogen,
  b) $C_{3-8}$ cycloalkyl,
  c) $C_{3-6}$ heterocyclyl,
  d) $C_{1-3}$ alkyl,
  e) $(C=O)C_{1-3}$ alkyl,
  f) aryl, and
  g) heteroaryl;
  wherein said cycloalkyl, heterocyclyl, alkyl, aryl and heteroaryl groups are each optionally substituted with one to three substituents independently selected from the group consisting of halo, hydroxyl, cyano, $R^8$, $SO_2R^8$, $OC_{1-6}$ alkyl and $C_{3-8}$ cycloalkyl;

or $R^c$ and $R^d$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of halo, cyano, hydroxyl, $C_{1-3}$ alkyl and $OC_{1-3}$ alkyl;

$R^e$ is selected from the group consisting of hydrogen and $C_{1-3}$ alkyl;
$R^f$ is selected from the group consisting of hydrogen and $C_{1-3}$ alkyl; and
m is an integer from zero to two.

In a class of the invention, $X^1$ is a bond. In another class of the invention, $X^1$ is $CR^eR^f$.

In a class of the invention, $X^2$ is a bond. In another class of the invention, $X^2$ is $CR^eR^f$.

In a class of the invention, $X^3$ is a bond. In another class of the invention, $X^3$ is $CR^eR^f$.

In a class of the invention, Y is O. In another class of the invention, Y is $CR^aR^b$. In another class of the invention, Y is $NR^c$.

In a class of the invention, Z is O. In another class of the invention, Z is $CR^aR^b$. In another class of the invention, Z is $NR^c$.

In a class of the invention, $R^1$ is selected from the group consisting of hydrogen and $C_{1-3}$ alkyl. In a subclass of the invention, $R^1$ is hydrogen. In another subclass of the invention, $R^1$ is methyl.

In a class of the invention, $R^2$ and $R^3$ are taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
  a) halo,
  b) oxo,
  c) cyano,
  d) $OR^5$,
  e) $NR^cR^d$,
  f) $SO_3H$
  g) $S(O)_mR^5$,
  h) $S(O)_mR^7$,
  i) $R^5$,
  j) $R^6$,
  k) $R^7$,
  l) $(C=O)R^5$,
  m) $(C=O)OR^5$,
  n) $(C=O)R^7$, and
  o) $(C=O)NR^cR^d$.

In a subclass of the invention, $R^2$ and $R^3$ can be taken together with the atoms to which they are attached to form a 6 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
  a) halo,
  b) oxo,
  c) $OR^5$,
  d) $NR^cR^d$,
  e) $S(O)_mR^5$,
  f) $S(O)_mR^7$,
  g) $R^5$,
  h) $R^6$,
  i) $R^7$,
  j) $(C=O)R^5$,
  k) $(C=O)OR^5$, and
  l) $(C=O)R^7$.

In a further subclass of the invention, $R^2$ and $R^3$ can be taken together with the atoms to which they are attached to form a morpholinyl group, which is optionally substituted with $C_{1-6}$ alkyl or $C_{1-6}$ alkylhydroxy. In a further subclass of the invention, $R^2$ and $R^3$ can be taken together with the atoms to which they are attached to form a piperazinyl group, which is optionally substituted with $C_{1-6}$ alkyl or $C_{1-6}$ alkyl-$SO_2$. In a further subclass of the invention, $R^2$ and $R^3$ can be taken together with the atoms to which they are attached to form a piperazinone group.

In a class of the invention, $R^4$ is selected from the group consisting of hydrogen and halo. In a subclass of the invention, $R^4$ is hydrogen.

In a class of the invention, $R^5$ is hydrogen.
In a class of the invention, $R^6$ is hydrogen.
In a class of the invention, $R^7$ is heterocyclyl.
In a class of the invention, $R^a$ is hydrogen.
In a class of the invention, $R^b$ is hydrogen.
In a class of the invention, $R^c$ is hydrogen.
In a class of the invention, $R^d$ is hydrogen.
In a class of the invention, $R^e$ is hydrogen.
In a class of the invention, $R^f$ is hydrogen.

Reference to the preferred classes and subclasses set forth above is meant to include all combinations of particular and preferred groups unless stated otherwise.

Specific embodiments of the present invention include, but are not limited to the compounds identified herein as Examples 1 to 37, or pharmaceutically acceptable salts thereof.

The invention also encompasses a pharmaceutical composition which comprises an inert carrier and the compound of Formula I, or a pharmaceutically acceptable salt thereof.

The invention may also encompass a method of treating Parkinson's Disease in a mammalian patient in need of such treatment, which comprises administering to the patient a therapeutically effective amount of the compound of Formula I, or a pharmaceutically acceptable salt thereof.

The invention may also encompass the use of a compound of Formula I, or a pharmaceutically acceptable salt thereof, and a pharmaceutically acceptable carrier, for the manufacture of a medicament for the treatment of Parkinson's Disease.

The invention is also directed to medicaments or pharmaceutical compositions which may be useful for treating diseases or disorders in which LRRK2 is involved, such as Parkinson's Disease, which comprise a compound of Formula I, or a pharmaceutically acceptable salt thereof, and a pharmaceutically acceptable carrier.

The invention is also directed to the use of a compound of Formula I which may be useful for treating diseases or disorders in which LRRK2 is involved, such as Parkinson's Disease.

The invention is further directed to a method for the manufacture of a medicament or a composition which may be useful for treating diseases or disorders in which LRRK2 is involved, such as Parkinson's Disease, comprising combining a compound of Formula I with one or more pharmaceutically acceptable carriers.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Unless a specific stereochemistry is indicated, the present invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Tautomers of compounds defined in Formula I are also included within the scope of the present invention. For example, compounds including carbonyl —CH2C(O)— groups (keto forms) may undergo tautomerism to form hydroxyl —CH=C(OH)— groups (enol forms). Both keto and enol forms are included within the scope of the present invention.

When any variable (e.g. $R^a$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be understood as meaning that the group in question is either unsubstituted or may be substituted with one or more substituents.

As used herein, "alkyl" is intended to mean linear or branched structures having no carbon-to-carbon double or triple bonds. Thus, $C_{1-4}$ alkyl is defined to identify the group as having 1, 2, 3 or 4 carbons in a linear or branched arrangement, such that $C_{1-4}$ alkyl specifically includes, but is not limited to, methyl, ethyl, n-propyl, iso-propyl, n-butyl, iso-butyl and tert-butyl.

As appreciated by those of skill in the art, "halo" or "halogen" as used herein is intended to include chloro (Cl), fluoro (F), bromo (Br) and iodo (I).

The term "cycloalkyl" shall mean cyclic rings of alkanes of three to eight total carbon atoms, unless otherwise indicated, or any number within this range (i.e., cyclopropyl, cyclobutyl, cyclopentyl, cyclohexyl, cycloheptyl, methyl-cyclopropyl, 2,2-dimethyl-cyclobutyl, 2-ethyl-cyclopentyl or cyclooctyl) and also includes bicyclic or fused spirocyclic compounds.

The term "cycloalkenyl" shall mean cyclic rings of four to eight total carbon atoms, unless otherwise indicated, or any number within this range where one or two degrees of unsaturation are present. Non-limiting examples of said cycloalkenyl groups are: cyclohexenyl, cyclopentenyl, cyclooctadienyl.

The term "carbocycle" shall mean cyclic rings of three to eight total carbon atoms, unless otherwise indicated, or any number within this range, where zero, one or two degrees of unsaturation are present and where said "carbocycle" can be bicyclic or fused spirocyclic in nature. Non-limiting examples of said carbocyclyl groups are: cyclohexenyl, cyclopentenyl, cyclooctadienyl, cyclohexyl or cyclopropyl.

If no number of carbon atoms is specified, the term "alkenyl" refers to a non-aromatic hydrocarbon radical, straight or branched, containing from 2 to 10 carbon atoms and at least 1 carbon to carbon double bond. Preferably 1 carbon to carbon double bond is present, and up to 4 non-aromatic carbon-carbon double bonds may be present. Thus, "C2-C6 alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

The term "heteroaryl", as used herein, represents a stable monocyclic, bicyclic or tricyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "heterocycle" or "heterocyclyl" as used herein is intended to mean a 5- to 10-membered nonaromatic ring, unless otherwise specified, containing from 1 to 4 heteroatoms selected from the group consisting of O, N, S, SO, or SO$_2$ and includes bicyclic groups. The heterocyclic group also includes rings that possess one or two degrees of unsaturation. "Heterocyclyl" therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Salts in the solid form may exist in more than one crystal structure, and may also be in the form of hydrates. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Salts derived from inorganic bases include aluminum, ammonium, calcium, copper, ferric, ferrous, lithium, magnesium, manganic salts, manganous, potassium, sodium, zinc, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which may be selected from the group consisting of the compounds disclosed in the following Examples and pharmaceutically acceptable salts thereof and individual diastereomers thereof.

The subject compounds are useful in a method of inhibition of LRRK2 receptors in a patient such as a mammal in need of such antagonism comprising the administration of an effective amount of the compound. The present invention is directed to the use of the compounds disclosed herein as inhibitors of LRRK2 receptors. In addition to primates, especially humans, a variety of other mammals can be treated according to the method of the present invention.

Another embodiment of the present invention is directed to a method for the treatment, control, amelioration, or reduction of risk of a disease or disorder in which the LRRK2 kinase is involved in a patient that comprises administering to the patient a therapeutically effective amount of a compound that is an inhibitor of LRRK2 kinase.

The present invention is further directed to a method for the manufacture of a medicament for inhibition of LRRK2 receptors activity in humans and animals comprising combining a compound of the present invention with a pharmaceutical carrier or diluent.

The subject treated in the present methods is generally a mammal, for example a human being, male or female, in whom inhibition of LRRK2 kinase activity is desired. The term "therapeutically effective amount" means the amount of the subject compound that will elicit the biological or medical response of a tissue, system, animal or human that is being sought by the researcher, veterinarian, medical doctor or other clinician.

The terms "treating" or "treatment" of a disease as used herein includes: inhibiting the disease, i.e., arresting or reducing the development of the disease or its clinical symptoms; or relieving the disease, i.e., causing regression of the disease or its clinical symptoms. The term "preventing" or "prevention" of a disease as used herein includes: causing the clinical symptoms of the disease not to develop in a mammal that may be exposed to or predisposed to the disease but does not yet experience or display symptoms of the disease, and the like.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The ability of the compounds of the present invention to act as LRRK2 kinase inhibitors may make them useful pharmacological agents for disorders that involve LRRK2 kinase in humans and animals, but particularly in humans.

In another embodiment the invention provides a method of inhibiting LRRK2 Kinase activity (this is to say, inhibiting the kinase activity associated with Leucine-Rich Repeat Kinase 2 [LRRK2], a multidomain protein containing kinase and GTPase enzymatic activities) in a patient in need of therapy for a condition amenable to treatment by such kinase activity inhibition, for example, treatment or prevention of neurologic damage associated with Parkinson's disease, for example, improvement in dopaminergic tone and in providing symptomatic benefit, for example, in treating, alleviating, ameliorating, or managing motor and non-motor symptoms of Parkinson's disease, and other conditions that may be treated or prevented by inhibition of LRRK2 kinase. Of particular importance is the acute or prophylactic treatment of Parkinson's Disease.

The subject compounds may be further useful in a method for the prevention, treatment, control, amelioration, or reduction of risk of the diseases, disorders and conditions noted herein.

The subject compounds may be further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with one or more additional therapeutic agents, for example: L-DOPA; dopaminergic agonists such as quinpirole, ropinirole, pramipexole, pergolide and bromocriptine; MAO-B inhibitors such as rasagiline, deprenyl and selegiline; DOPA decarboxylase inhibitors such as carbidopa and benserazide; and COMT inhibitors such as tolcapone and entacapone; or potential therapies such as an adenosine A2a antagonists, metabotropic glutamate receptor 4 modulators, or growth factors such as brain derived neurotrophic factor (BDNF), and a pharmaceutically acceptable carrier.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, buccal or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require inhibition of LRRK2 kinase activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of Parkinson's Disease, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

General Schemes

A general procedure for the preparation of cycloalkoxy substituted indazoles such as Formula I is shown in Scheme 1. Treatment of a suitable bromo-indazole i with iodine/KOH and the like will provide compound ii. The indazole can be protected with SEMCl and the like to provide the protected indazole iii. The iodo group in iii can be coupled with a boronic acid iv and the like to provide indazole v. The bromide in v can be converted into the pinacol boronic ester vii using vi under palladium catalyzed conditions and the like. The boronic ester v can be oxidized to the alcohol viii using acetic acid/$H_2O_2$ and the like. The alcohol in viii can be reacted with electrophiles (LG=leaving group) such as ix in the presence of $K_2CO_3$ followed by removal of the indazole protecting group with TBAF and the like to provide examples such as Formula I. Alternatively, the SEM protecting group can removed by a two step method wherein the starting material is first treated with a mixture such as TFA in CH2Cl2 and the like followed by concentration and treatment of the residue with ammonium hydroxide and the like.

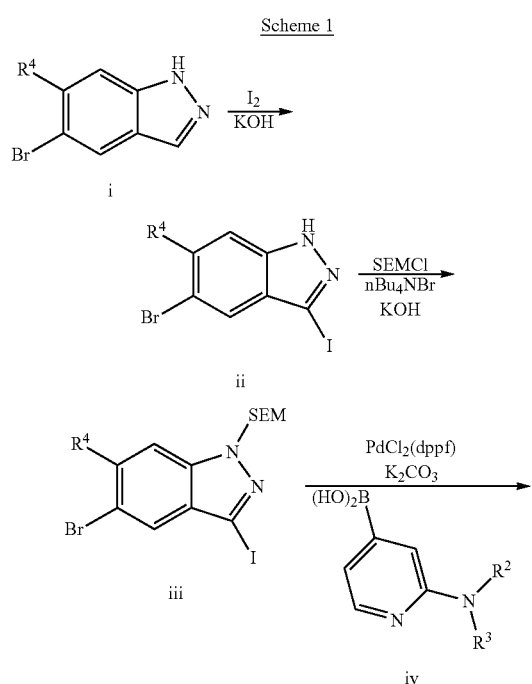

Scheme 1

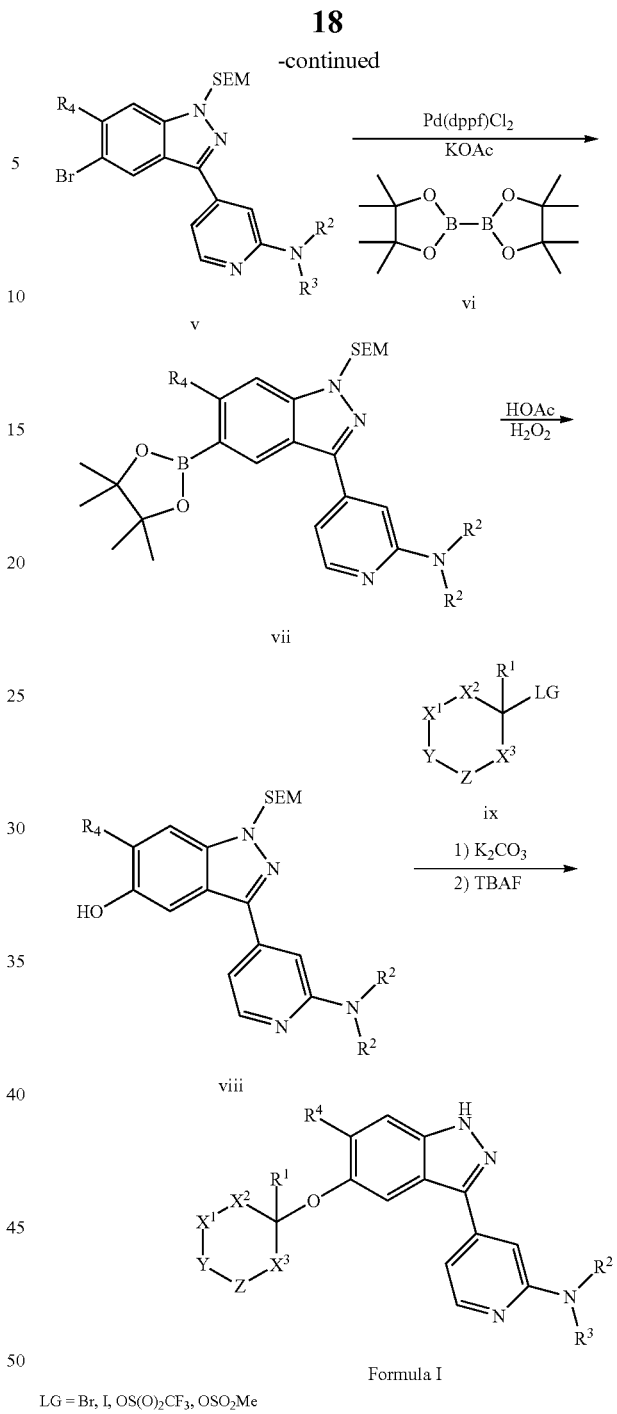

LG = Br, I, OS(O)$_2$CF$_3$, OSO$_2$Me

Alternatively, treatment of i with NIS followed by a base such as NaH and the like and TrCl will provide xi. The iodo indazole xi can be converted into the pyridyl substituted indazole xii via palladium-catalyzed cross coupling with a boronic acid or ester such as iv and the like. The aryl bromide xii can be converted into the alcohol xiii by first conversion to the pinacol boronate via pinacol diborane and a palladium catalyst and the like, followed by oxidation of the pinacol boronate with hydrogen peroxide/acetic acid and the like. The alcohol xiii can be converted into examples such as Formula I using a base such as cesium carbonate and the like and an appropriate electrophile ix (LG=leaving group) and the like followed by removal of the trityl group with a mixture of triethylsilane/TFA and the like. Alternatively, the trityl group can be removed with a mixture of hydrogen chloride in methanol.

Treatment of xiv with an appropriate alcohol xv and base and the like will provide the ether xvi. The bromide xvi can be converted into the methylated intermediate xvii using palladium catalyst and $Me_3B_3O_3$ and the like. The nitro derivative xvii can be treated with Pd/C in the presence of $HCOONH_4$ to produce the amine xvii. The amine xvii can be acylated to provide xix. The acylated amine xix can be treated with iso-amyl nitrate in the presence of $Ac_2O/KOAc$ and the like to provide the indazole xx. The indazole can be treated with ammonia and the like to produce xxi. The indazole xxi can be treated with iodine and KOH and the like to provide the iodo-indazole xxii. The indazole can be protected with trityl chloride and base and the like to provide xxiii. The iodo-indazole xxiii can be converted into xxiv using the appropriate boronic acid and palladium catalyst and the like. The chloro-pyridine xxiv can be converted into examples such as Formula I using the appropriate amine $(HN(R^2)R^3)$, palladium catalyst, and ligand followed by deprotection of the trityl group using standard conditions.

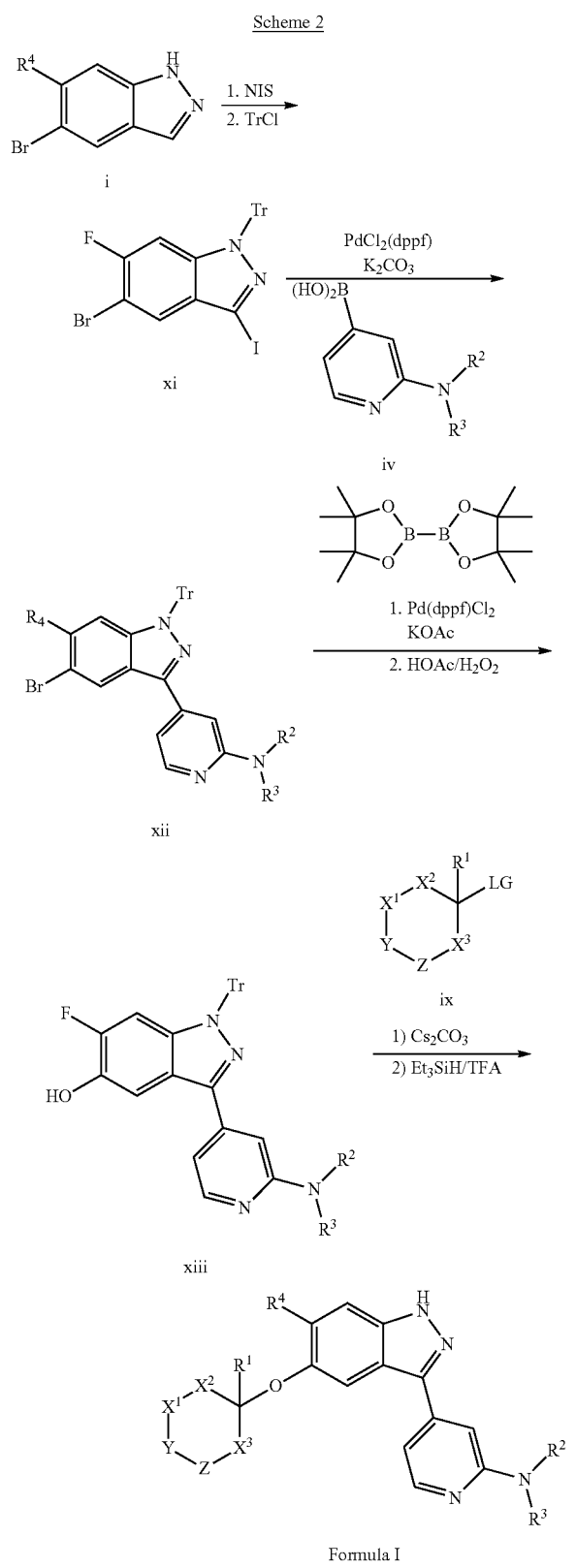

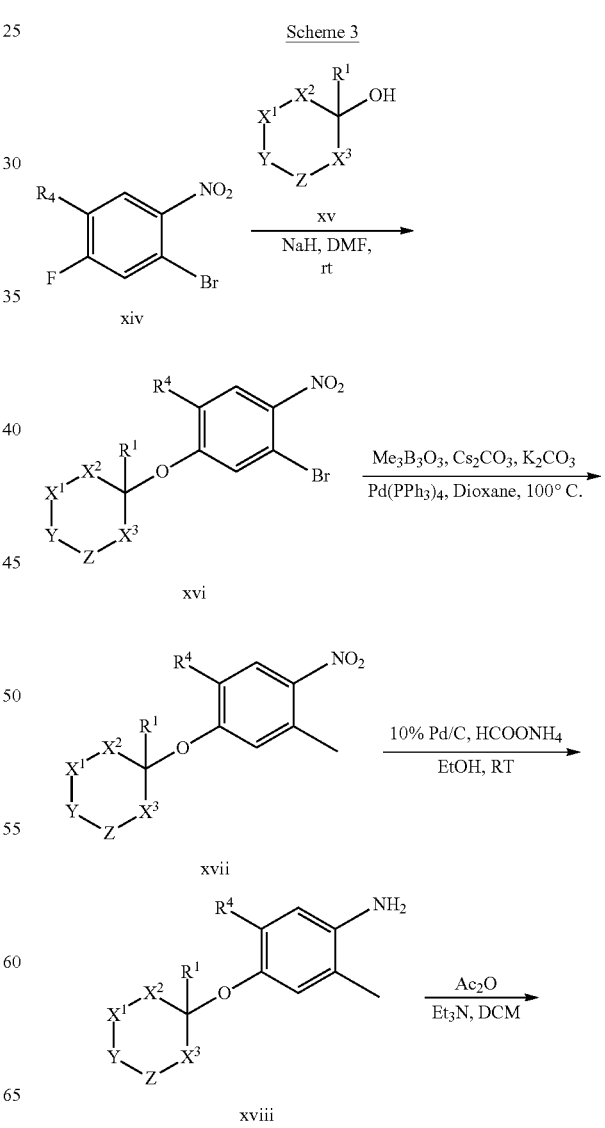

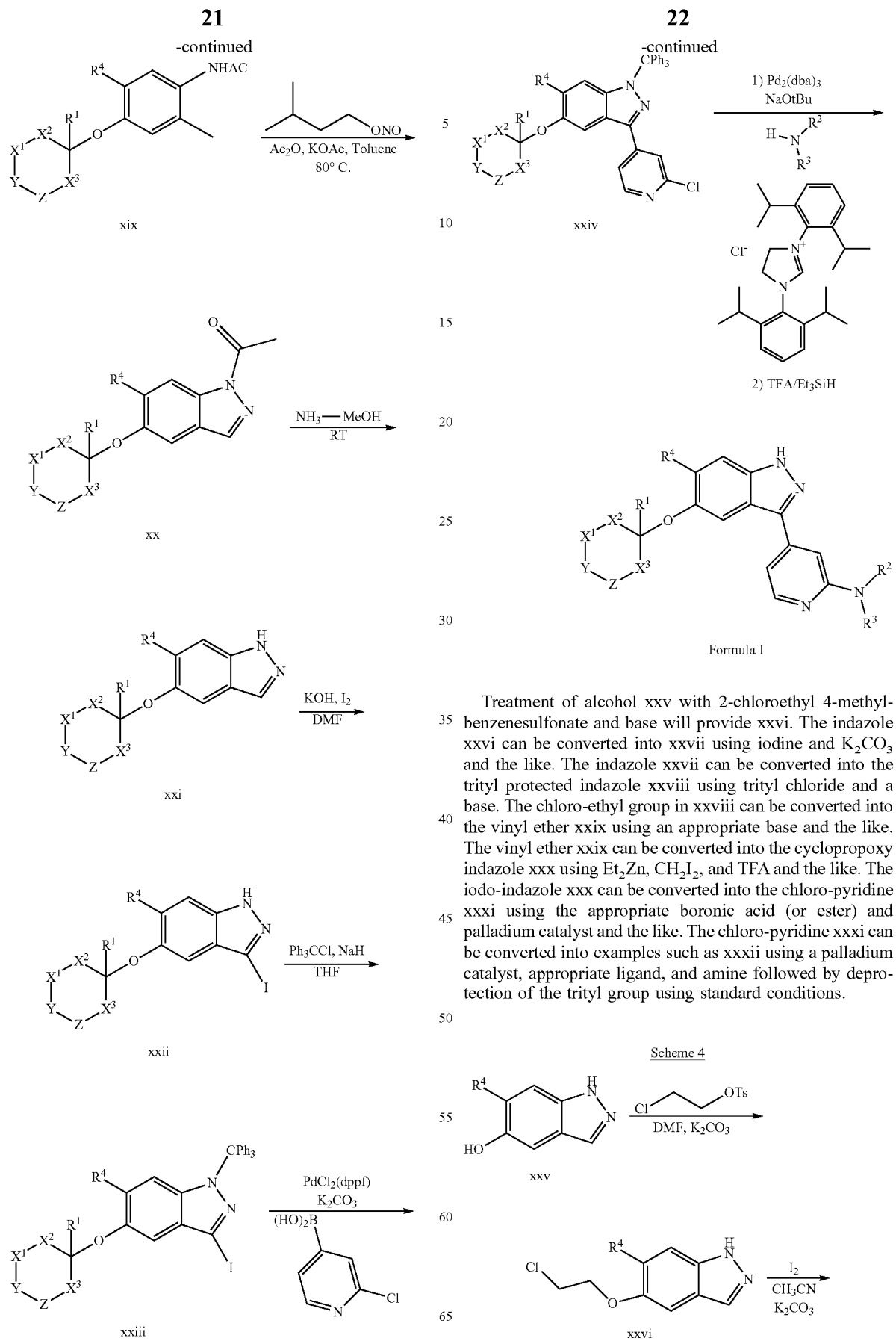

Treatment of alcohol xxv with 2-chloroethyl 4-methyl-benzenesulfonate and base will provide xxvi. The indazole xxvi can be converted into xxvii using iodine and $K_2CO_3$ and the like. The indazole xxvii can be converted into the trityl protected indazole xxviii using trityl chloride and a base. The chloro-ethyl group in xxviii can be converted into the vinyl ether xxix using an appropriate base and the like. The vinyl ether xxix can be converted into the cyclopropoxy indazole xxx using $Et_2Zn$, $CH_2I_2$, and TFA and the like. The iodo-indazole xxx can be converted into the chloro-pyridine xxxi using the appropriate boronic acid (or ester) and palladium catalyst and the like. The chloro-pyridine xxxi can be converted into examples such as xxxii using a palladium catalyst, appropriate ligand, and amine followed by deprotection of the trityl group using standard conditions.

Scheme 4

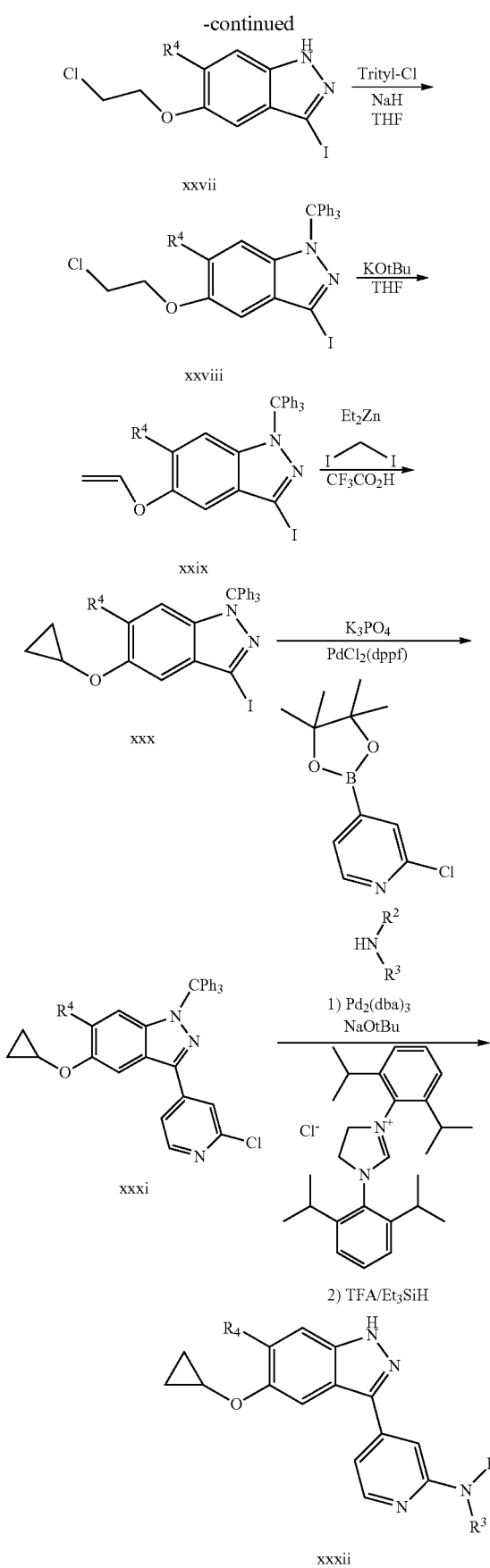

Treatment of indazole ii with SEMCl and a base will provide the SEM protected indazole iii. The iodo-indazole iii can be converted into the fluoro-pyridine xxxiii using an appropriate palladium catalyst and boronic acid and the like. The fluoro-pyridine xxxiii can be converted into the amino-pyridine xxxiv using the appropriate amine (HN(R²)R³) and base under standard conditions. The bromo-indazole xxxiv can be converted into the boronic ester vii using pinacol diborane and the appropriate palladium catalyst and the like. The boronate ester vii can be oxidized to the alcohol viii using standard conditions such as $H_2O_2$ in acetic acid. The alcohol viii can be reacted with an appropriate electrophilic reagent (where LG=leaving group) and base to provide xxxiv using standard conditions. Treatment of xxxiv with TFA will provide examples such as Formula I.

Scheme 5

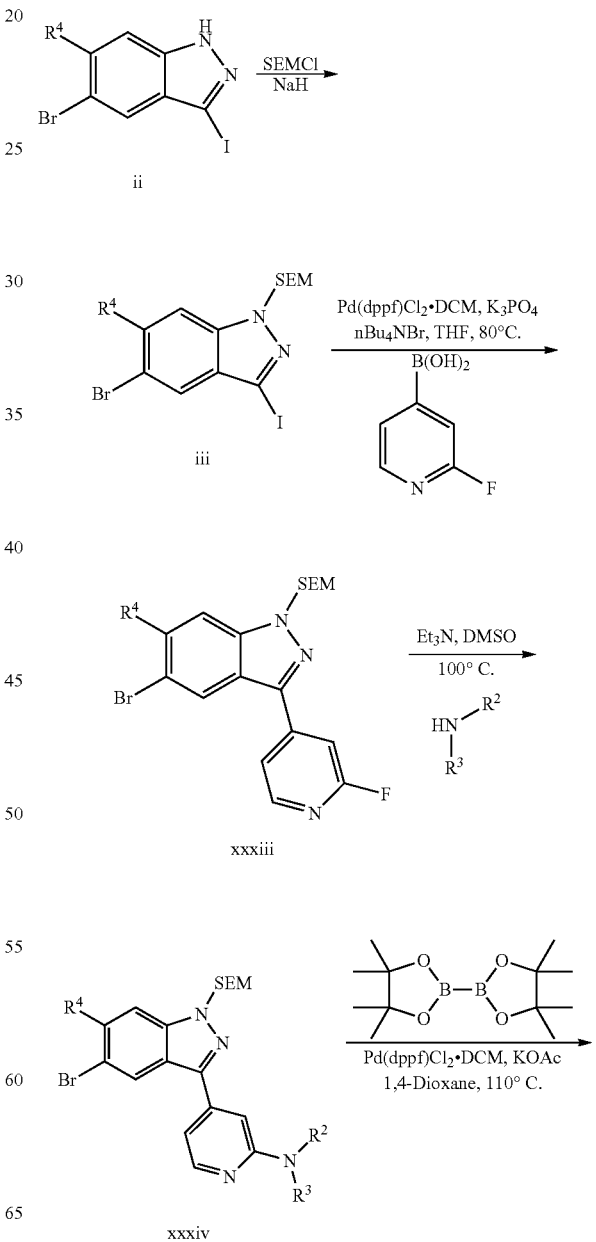

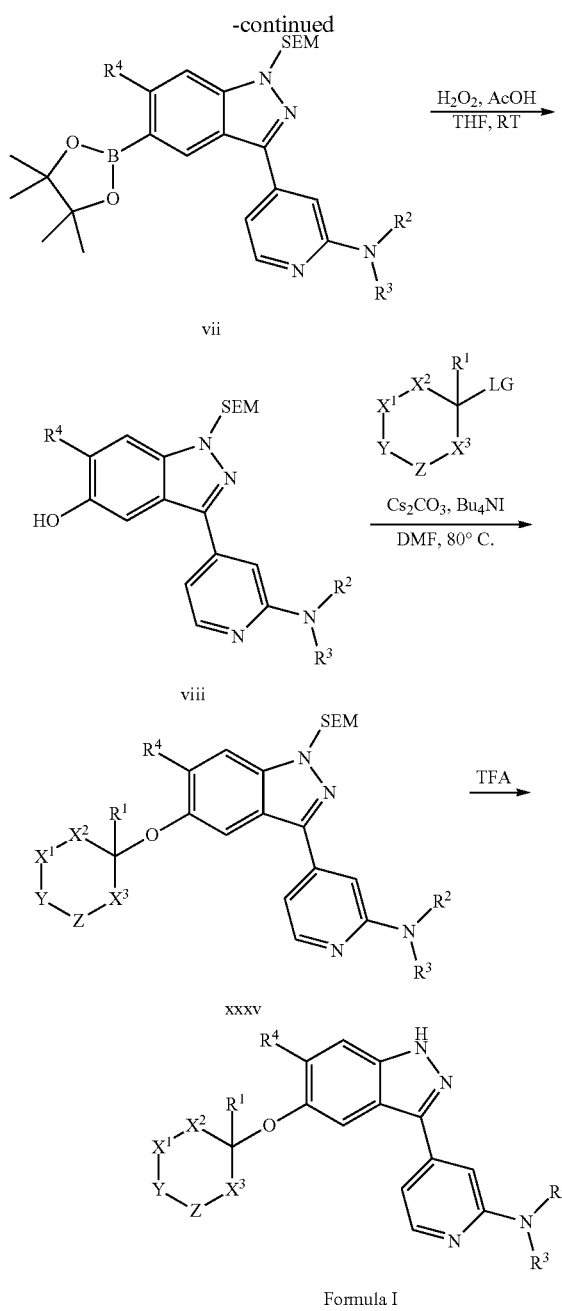

Formula I

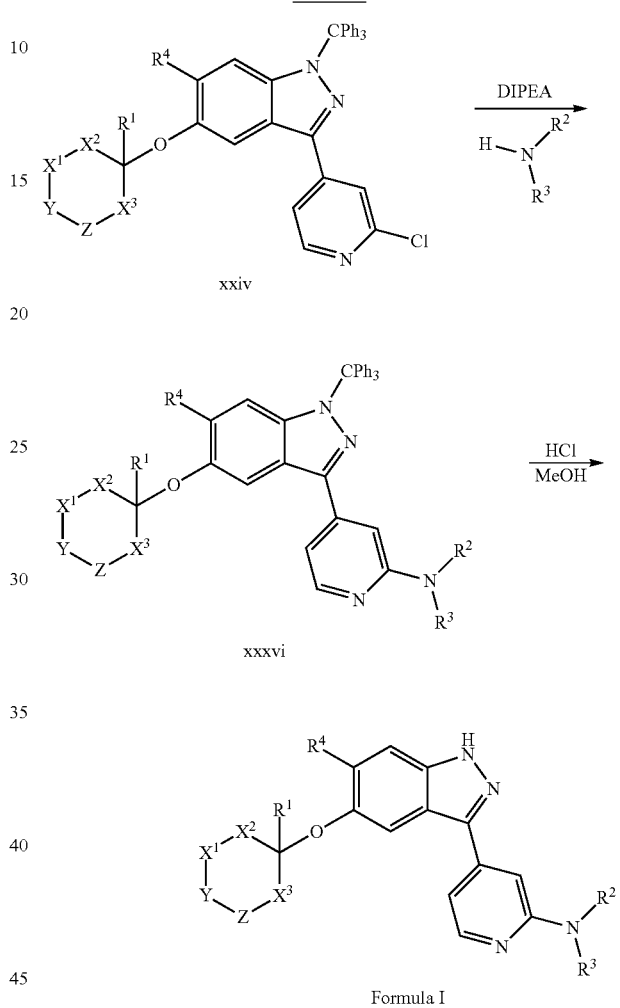

The chloro-pyridine xxiv can be reacted with an amine (HN($R^2$)$R^3$) and appropriate base to provide xxxvi using standard conditions. The trityl protected indazole xxxvi can be converted into examples such as Formula I using HCl in MeOH and the like.

Experimentals

Abbreviations used in the experimentals may include the following:

| | | | |
|---|---|---|---|
| ACN | Acetonitrile | AcOH | Acetic acid |
| Aq | Aqueous | Bn | Benzyl |
| BOC | tert-Butoxycarbonyl | $BOC_2O$ | BOC Anhydride |
| Bu | Butyl | C. (or ° C.) | degrees Celsius |
| Cbz | benzyloxycarbonyl | DBU | 1,8-Diazabicyclo[5.4.0]undec-7-ene |
| DCM | Dichloromethane | DIPEA | Diisopropylethylamine |
| DMA | N,N-Dimethylacetamide | DMAP | 4-Dimethylaminopyridine |
| DME | 1,2-dimethoxyethane | DMF | Dimethylformamide |
| DMSO | Dimethyl sulfoxide | DPPF | 1,1'-(bis-diphenylphosphino) ferrocene |
| EDCI | 1-(3-Dimethylaminopropyl)-3-ethylcarbodiimide hydrochloride | EDC | 1-(3-Dimethylaminopropyl)-3-ethylcarbodiimide hydrochloride |
| EI | Electron ionization | Eq | Equivalents |
| Et | Ethyl | EtOAc | Ethyl acetate |

-continued

| | | | |
|---|---|---|---|
| EtOH | Ethanol | g | grams |
| h, hr | hours | ¹H | proton |
| HATU | N,N,N',N'-Tetramethyl-O-(7-Azabenzotriazol-1-yl)uronium hexafluorophosphate | Hex | hexanes |
| HOBT | 1-Hydroxybenzotriazole | HOBT•H₂O | 1-Hydroxybenzotriazole hydrate |
| HOTS | para-toluene sulfonic acid (see also TsOH) | HOTS•H₂O | para-toluene sulfonic acid hydrate (see also TsOH•H₂O) |
| HMPA | hexamethylphosphoramide | HPLC | High pressure liquid chromatography |
| IPA | isopropanol, 2-propanol | LDA | lithium diisopropylamide |
| M | Molar | mmol | milimolar |
| mCPBA | meta-Chloroperoxy benzoic acid | Me | Methyl |
| MeCN | Acetonitrile | MeOH | Methanol |
| min | Minutes | mg | Milligrams |
| MHZ | Megahertz | mL (or ml) | Milliliter |
| Mol sieves | molecular sieves | N | normal |
| NMR | Nuclear Magnetic Resonance | MS | Mass Spectroscopy |
| NBS | N-Bromosuccinimide | NMM | N-Methylmorpholine |
| NMP | 1-methyl-2-pyrrolidone | ON | Overnight |
| PTLC | Preparative thin layer chromatography | PyBrOP | Bromo-tris-pyrrolidino-phosphonium hexafluorophosphate |
| PyBOP | (Benzotriazol-1-yloxy)tripyrrolidinophosphonium hexa-fluorophosphate | Pyr | Pyridine |
| Quant | quantitative | RT or rt | Room temperature |
| sat (or sat. or sat'd.) | Saturated | SFC | supercritical fluid chromatography |
| sgc | Silica gel 60 chromatography | SiO₂ | Silica gel |
| tBOC | tert-Butoxycarbonyl | t-Bu | tert-butyl |
| TEA | Triethylamine | Tf | Trifluoromethane sulfonyl |
| TFA | Trifluoroacetic acid | THF | Tetrahydrofuran |
| TLC | Thin layer chromatography | Ts | Toluene sulfonyl |
| TsOH | para-toluene sulfonic acid | TsOH•H₂O | para-toluene sulfonic acid hydrate |

General Experimental Information:

Unless otherwise noted, all reactions are magnetically stirred.

Unless otherwise noted, when ethyl acetate, hexanes, dichloromethane, 2-propanol, and methanol are used in the experiments described below, they are Fisher Optima grade solvents.

Unless otherwise noted, when diethyl ether is used in the experiments described below, it is Fisher ACS certified material and is stabilized with BHT.

Unless otherwise noted, "concentrated to dryness" means evaporating the solvent from a solution or mixture using a rotary evaporator.

Unless otherwise noted, flash chromatography is carried out on an Isco, Analogix, or Biotage automated chromatography system using a commercially available cartridge as the column. Columns may be purchased from Isco, Analogix, Biotage, Varian, or Supelco and are usually filled with silica gel as the stationary phase.

Unless otherwise noted, all LRRK2 IC$_{50}$ data presented in tables refers to the LRRK2 Km ATP LanthaScreen™ Assay that is described in the Biological Assay section.

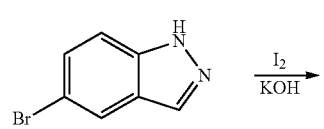

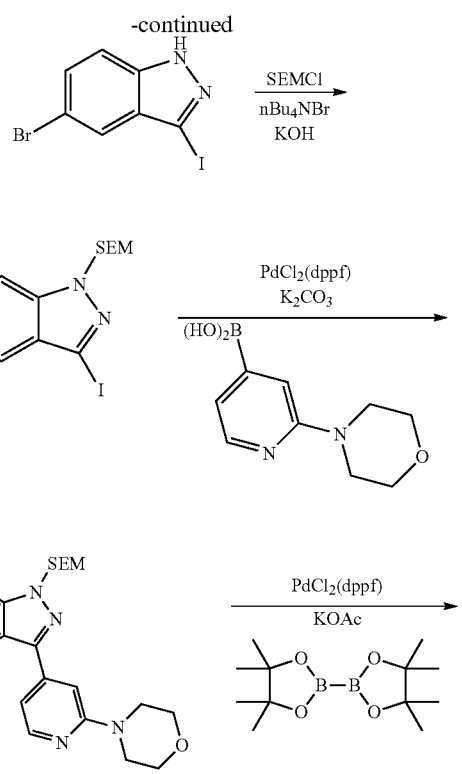

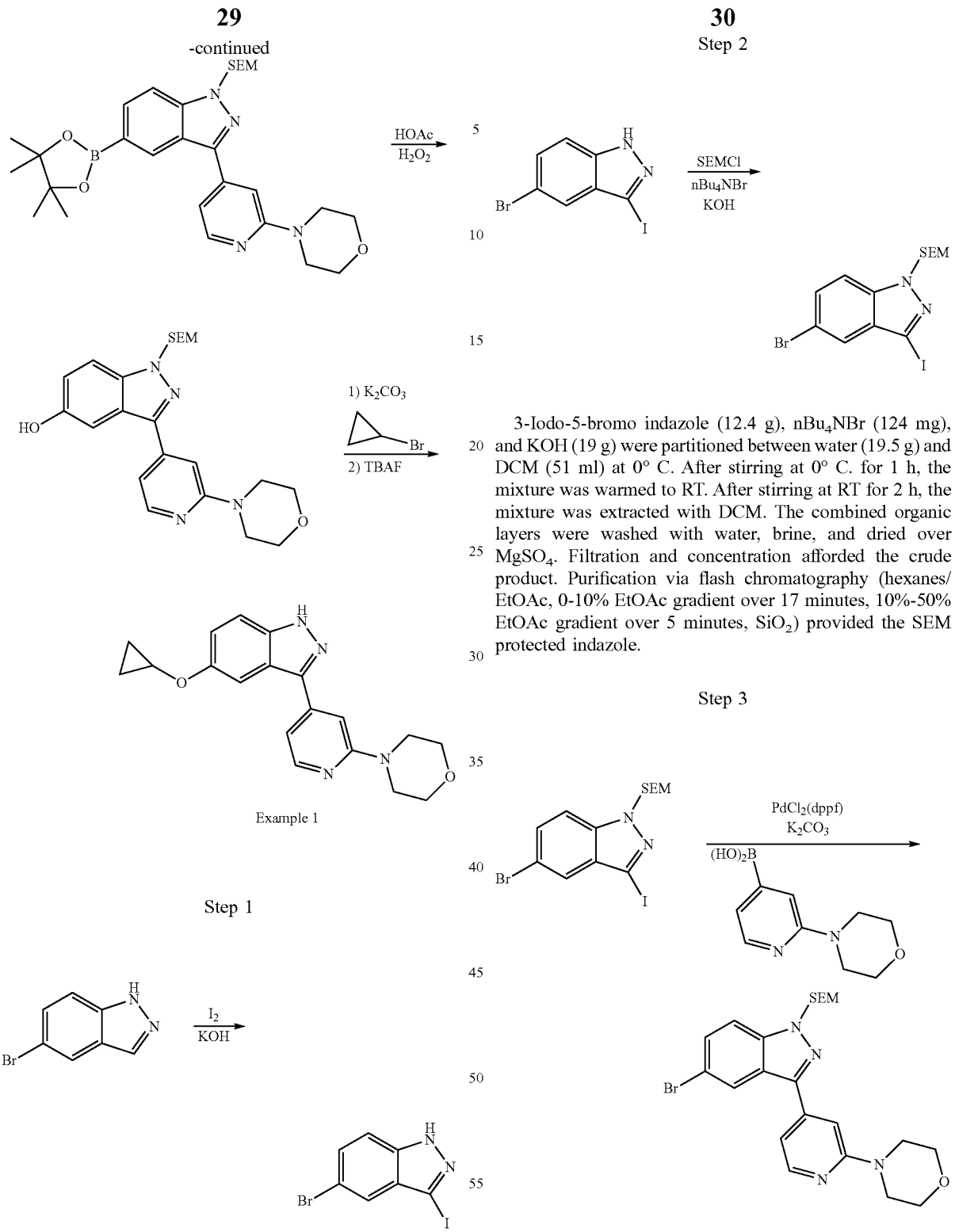

Step 2

3-Iodo-5-bromo indazole (12.4 g), nBu₄NBr (124 mg), and KOH (19 g) were partitioned between water (19.5 g) and DCM (51 ml) at 0° C. After stirring at 0° C. for 1 h, the mixture was warmed to RT. After stirring at RT for 2 h, the mixture was extracted with DCM. The combined organic layers were washed with water, brine, and dried over MgSO₄. Filtration and concentration afforded the crude product. Purification via flash chromatography (hexanes/EtOAc, 0-10% EtOAc gradient over 17 minutes, 10%-50% EtOAc gradient over 5 minutes, SiO₂) provided the SEM protected indazole.

Step 3

Step 1

5-Bromoindazole (10 grams) and KOH (5.7 g) were taken up in DMF (83 ml) at RT. Iodine (19.3 g) was added, and the resulting solution was stirred at RT for 24 h. The solution was diluted with EtOAc and 10% NaHSO₃ (aq.). The aqueous layer was extracted with EtOAc. The combined organic layers were washed with water, brine, and dried over MgSO₄. Filtration and concentration afforded 3-iodo-5-bromoindazole.

The SEM protected indazole (2.1 g), PdCl₂(dppf) (360 mg), K₂CO₃ (1.2 g), and boronic acid (918 mg) were taken up in dioxane/water (20 ml/2 ml), and the resulting solution was stirred at 100° C. for 2 h. The mixture was extracted with EtOAc. The combined organic layers were washed with water, brine, and dried over Na₂SO₄. Filtration and concentration gave the crude product. Purification via flash chromatography (0-3% MeOH in DCM gradient, SiO₂) provided the desired arylated indazole.

Step 4

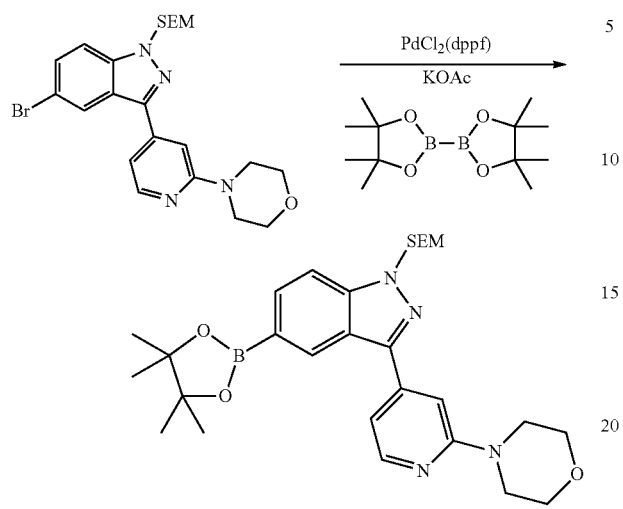

The bromo indazole (500 mg), pinacol diborane (389 mg), PdCl₂(dppf) (166 mg and KOAc (400 mg) were taken up in dioxane (10 ml), and the resulting solution was microwaved at 120° C. for 20 minutes. The solution was concentrated, and the residue was purified via flash chromatography (0-3% MeOH in DCM gradient, SiO₂) which provided the boronate as a yellow solid.

Step 5

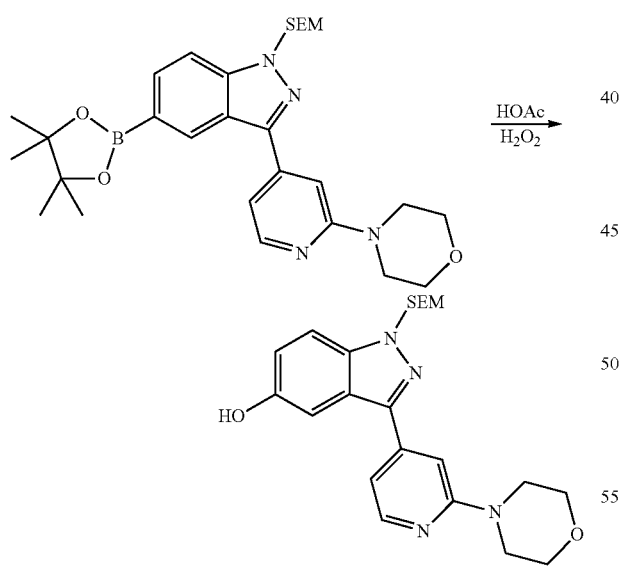

The boronate (200 mg) was taken up in 2 ml of THF. Acetic acid (50 µL) and H₂O₂ (180 µL of 50% in water) were added, and the resulting solution was stirred at RT for 1 h. Another portion of acetic acid/hydrogen peroxide was added. After stirring at RT for one hour, another portion of acetic acid/hydrogen peroxide was added, and the resulting solution was stirred at RT for 24 h. The solution was concentrated and partitioned between sat. NaHCO₃ $_{(aq.)}$/ ether. The aqueous layer was extracted with ether. The combined ether layers were dried (Na₂SO₄), filtered, and concentrated to afford the phenol as a yellow solid.

Step 6

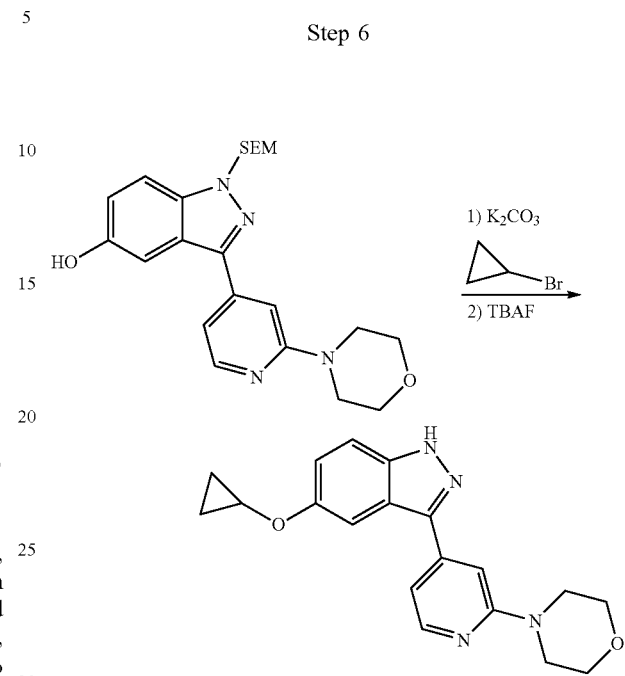

Example 1

The phenol (130 mg), K₂CO₃ (136 mg), and cyclopropyl bromide (119 mg) were taken up in DMF (1 ml), and the solution was heated at 100° C. for 3 days. The DMF was removed under reduced pressure. The residue was purified via preparative thin-layer chromatography (1/1 hexanes/ EtOAc, SiO₂) provided Example 1 as a yellow solid.

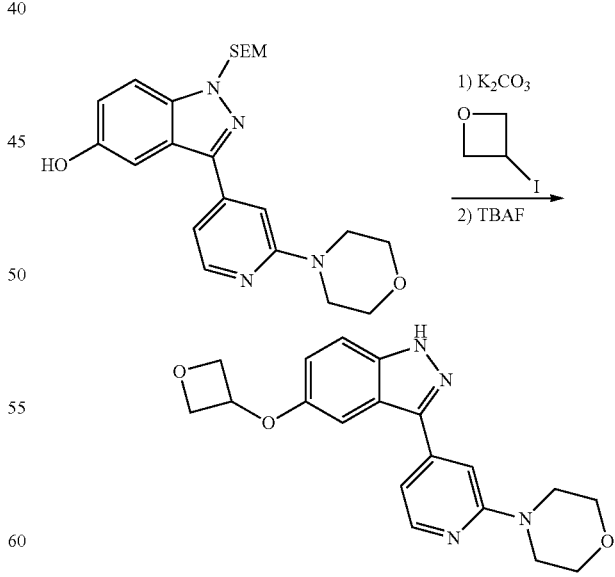

Example 2

The phenol (Step 5 of Scheme A) was converted into Example 2 using conditions similar to those outlined in Step 6 of Scheme A.

Scheme C

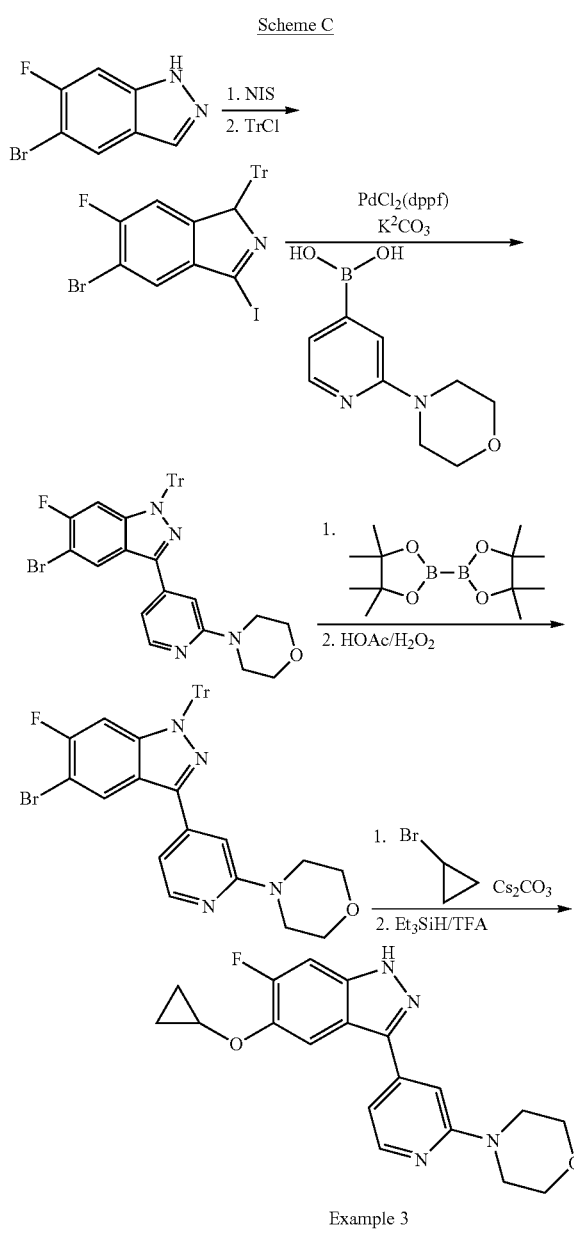

Example 3

Step 1

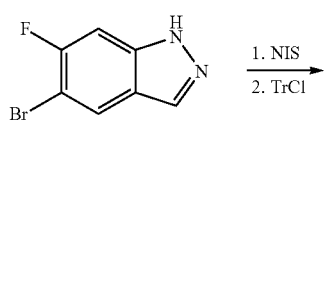

5-Bromo-6-fluoro indazole (2 g) and NIS (2.5 g) were taken up in CH$_3$CN (15 ml) and the solution was heated in a microwave at 105° C. for 30 minutes. The solution was concentrated. The residue was taken up in DCM (30 ml), and TrCl (3.9 g) and TEA (1.9 g) were added. The solution was stirred at RT for 48 h and then at 40° C. for 3 hr. The solution was concentrated. Purification via flash chromatography (0-20% DCM in hexanes gradient, SiO$_2$) provided the iodide as a yellow solid.

Steps 2 and 3

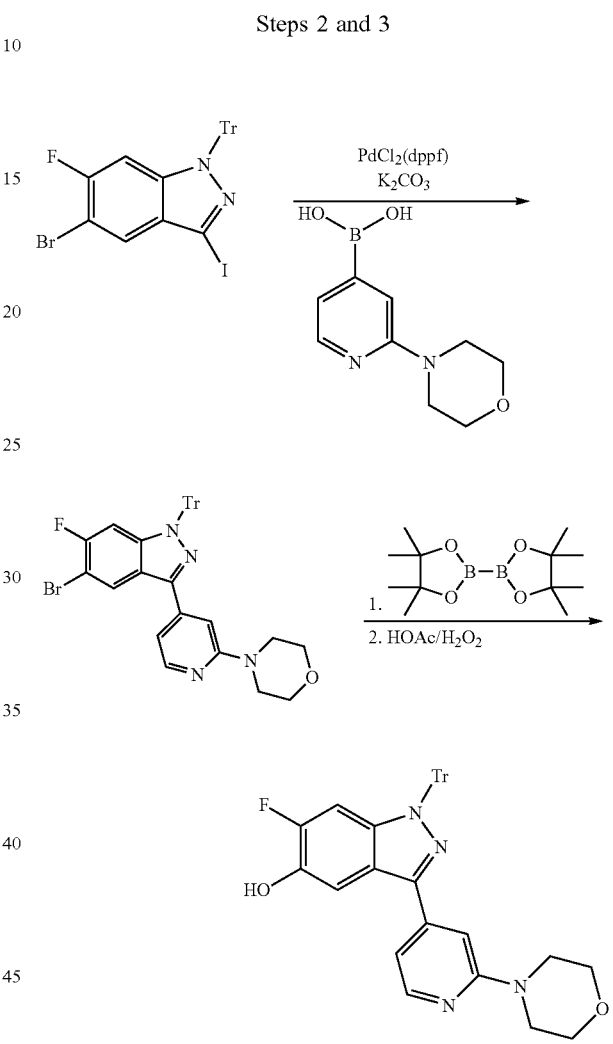

The iodide was converted into the phenol using conditions outlined in Scheme A.

Step 4

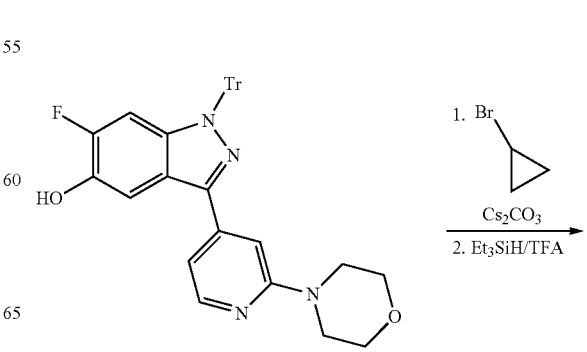

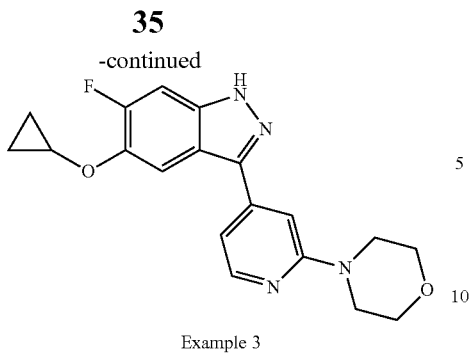

Example 3

The phenol (30 mg), Cs₂CO₃ (123 mg) and cyclopropyl bromide (39 mg) were taken up in DMSO (1 ml), and the resulting solution was subjected to microwave conditions (200° C. for 1 h). The mixture was filtered, and the solution was concentrated. The residue was treated with 1.5 ml of TFA and 0.5 ml of Et₃SiH. The solution was stirred at RT for 10 minutes after which DCM (1 ml) was added. The resulting solution was stirred at RT for 2 h. The solution was concentrated and 7 N NH₃ in MeOH was added (5 ml). The solution was concentrated. The residue was purified via thin layer preparative chromatography (5% MeOH in DCM, SiO₂) which provided Example 3 as a yellow solid.

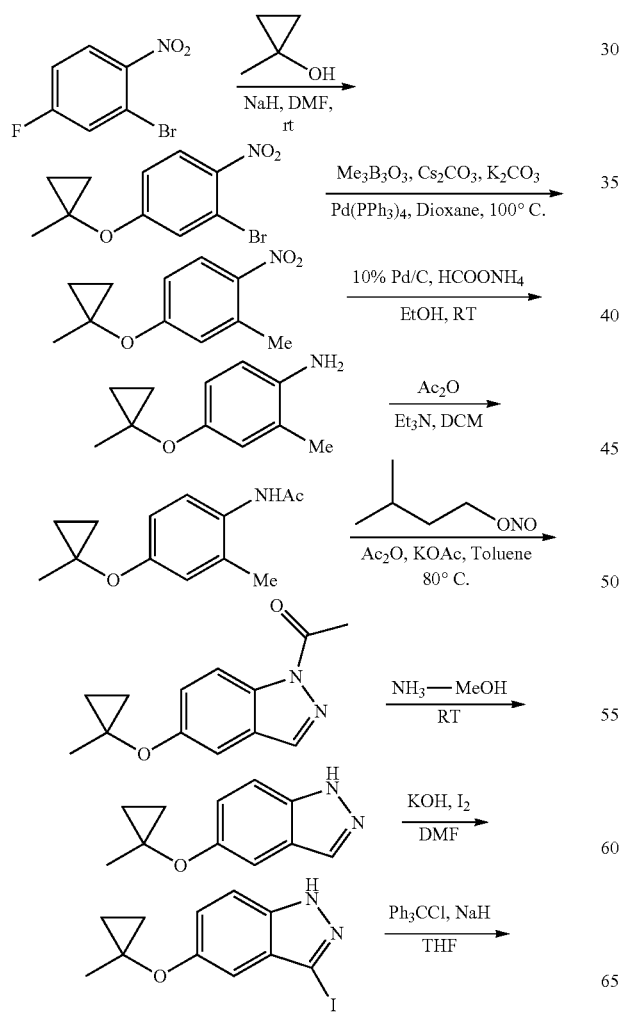

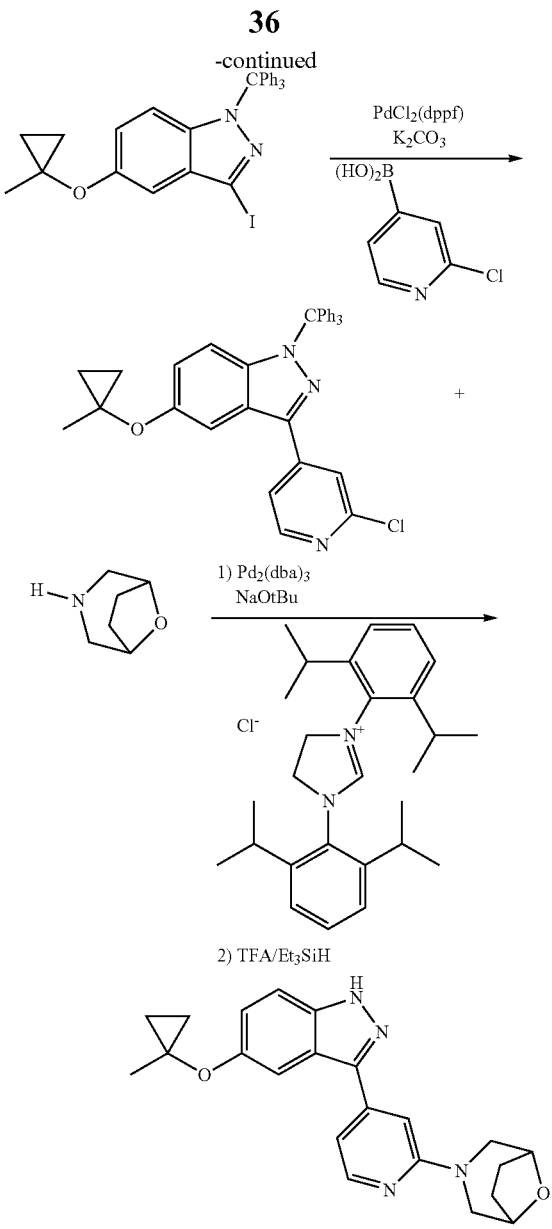

Example 4

Step 1

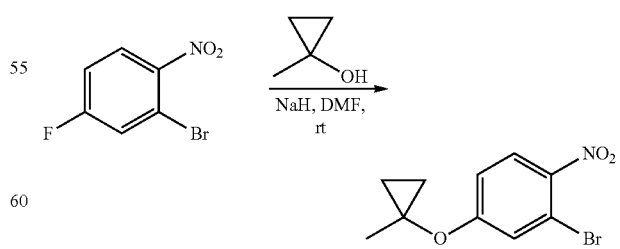

To a cold (0° C.), stirred mixture of 2-bromo-4-fluoronitrobenzene (10.0 g, 45.5 mmol) and 1-methylcyclopropanol (3.61 g, 50.0 mmol) in DMF (200 ml) was added NaH (2.36 g of 60% in oil, 59.1 mmol) in portions. Once the addition was complete the cold bath was removed and the mixture was stirred at rt for 5 h. The reaction was quenched with water and extracted with EtOAc (×3). The combined organic layers were washed with water (×3), brine (×2), dried, filtered and concentrated to leave an oil which was purified by column chromatography (elution with 100:0 to 20:1 hexane:EtOAc) to yield the desired product as a light yellow oil.

Step 2

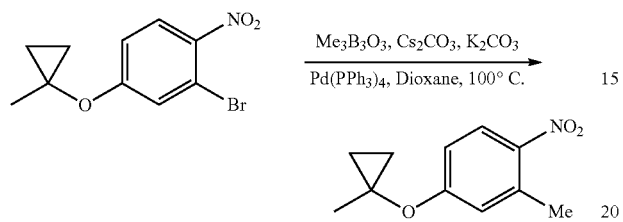

To a stirred mixture of the ether (2.0 g, 7.35 mmol), K₂CO₃ (2.03 g, 14.70 mmol) and Cs₂CO₃ (2.39 g, 7.35 mmol) in Dioxane (110 ml) was purged Ar for 15 min. Then trimethylborazine (2.26 ml, 16.17 mmol) and Pd(Ph₃P)₄ (0.85 g, 0.74 mmol) were added and the mixture was heated at 100° C. overnight. The reaction was cooled to room temperature and concentrated under vacuum. To this residue was added 10:1 hex:EtOAc (500 mL) and filtered through a pad of silica. The solid was washed with a mixture of hexane:EtOAc (1 L of 10:1 hexane:EtOAc) solution. The filtrate was concentrated under vacuum to provide the desired product, which was used in the next step without further purification.

Step 3

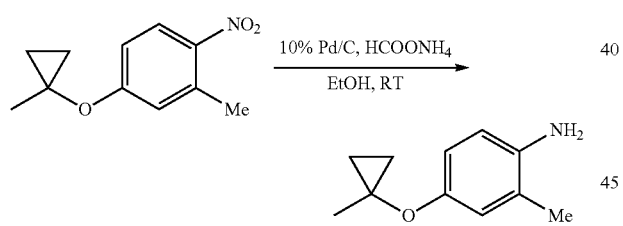

The nitro derivative was dissolved in absolute EtOH (110 mL). To this solution were added 10% Pd/C (0.782 g, 0.735 mmol) and ammonium formate (5.56 g, 88.0 mmol) and the mixture was stirred at room temperature for 5 h. To this solution was added a solution containing 5:1 hexane:EtOAc (500 mL) and the mixture was filtered through a pad of silica. The filtrate was concentrated and the residue was purified by column chromatography (elution with 10:1 to 5:1 hexane:EtOAc) to yield the desired amine as a dark brown oil.

Step 4

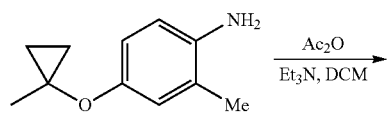

-continued

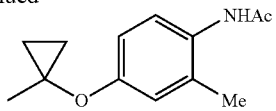

To a cold (0° C.), stirred mixture of amine (1.4 g, 7.90 mmol) and triethylamine (2.20 ml, 15.80 mmol) in CH₂Cl₂ (12 ml) was added Ac₂O (1.12 ml, 11.85 mmol). The mixture was slowly warmed to room temperature and stirred overnight. Silica gel was added and the mixture was evaporated to leave a slurry which was then purified by column chromatography (elution with 1:1 hexane:EtOAc) to yield the desired acetamide as a colorless gum.

Step 5

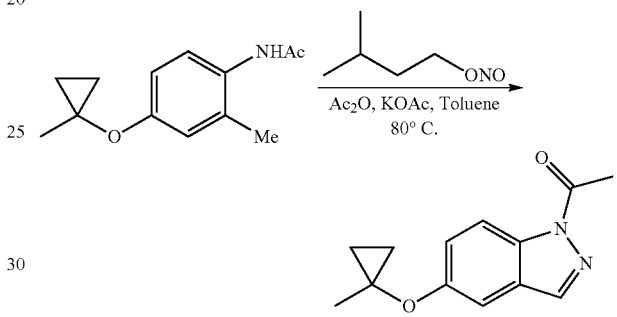

To a stirred solution of the acetamide (1.76 g, 8.03 mmol) in toluene (42 ml) were added KOAc (1.182 g, 12.04 mmol) and Ac₂O (3.48 ml, 36.9 mmol). Then the mixture was heated to 80° C. when isoamyl nitrite (4.49 ml, 32.1 mmol) was added dropwise and the resulting mixture was heated at 80° C. overnight. The insoluble material was filtered through a pad of celite and the filtrate was concentrated to leave a residue which was purified by column chromatography (elution with 20:1 hexane:EtOAc) to yield the desired product as a yellow solid.

Step 6

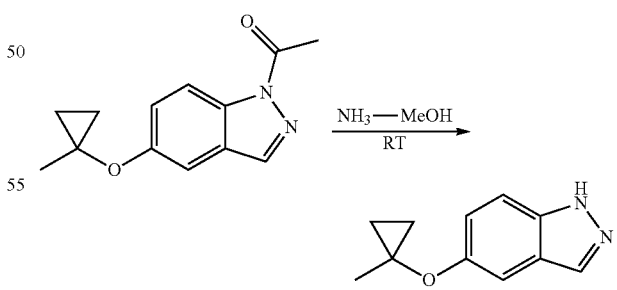

To a stirred suspension of the N-acetyl indazole (6.5 g, 28.2 mmol) in MeOH (20 mL) was added NH₃ (20.16 ml of 7M solution in MeOH, 141.0 mmol) and the mixture was stirred at RT for 2 h. The reaction was concentrated and the residue was purified by column chromatography (elution with 5:1 to 1:1 hexane:EtOAc) to yield the desired indazole as a yellow solid.

Step 7

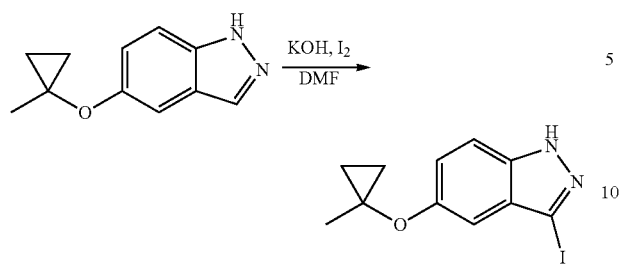

To a stirred solution of indazole (5.0 g, 26.6 mmol) in DMF (50 ml) was added KOH (5.96 g, 106 mmol) followed by I$_2$ (13.48 g, 53.1 mmol). The mixture was stirred at room temperature for 3 h before being quenched with a saturated aqueous solution of Na$_2$S$_2$O$_3$ followed by addition of water. The resulting layer was extracted with EtOAc (×4). The combined organic layers were dried over MgSO$_4$, filtered and concentrated under vacuum to leave a residue which was purified by column chromatography (elution with 10:1 to 1:1 hexane:EtOAc) to yield the iodide as a yellow solid.

Step 8

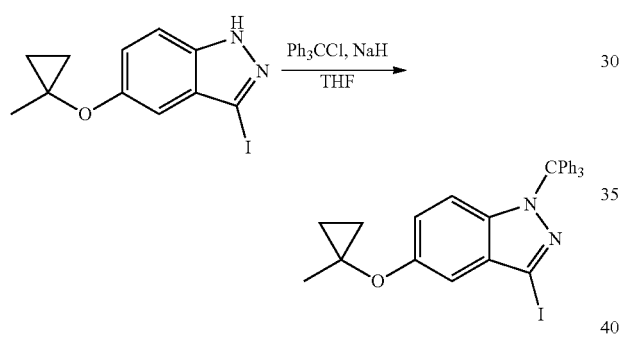

To a cold (0° C.), stirred solution of iodide (5.1 g, 16.24 mmol) in THF (50 ml) was added NaH (0.779 g, 19.48 mmol) in portions. After the addition was complete the mixture was stirred at 0° C. for 15 min when trityl chloride (4.98 g, 17.86 mmol) was added in one portion. The resulting mixture was then slowly warmed to room temperature and stirred at room temperature for 4 h. The reaction was quenched with water and extracted with DCM (×3). The combined organic layers were dried over MgSO$_4$, filtered and concentrated to leave a residue which was purified by column chromatography (elution with 100% DCM) to yield the desired product as an off-white solid.

Step 9

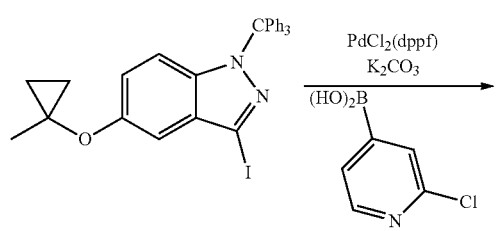

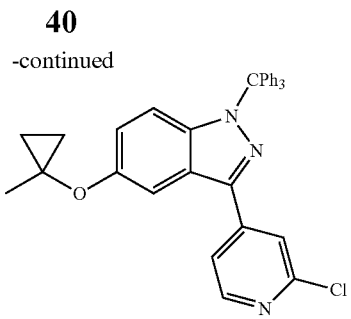

The iodide was reacted with (2-chloropyridin-4-yl)boronic acid using conditions outlined in Step 3 of Scheme A which provided the desired chloro-pyridine.

Step 10

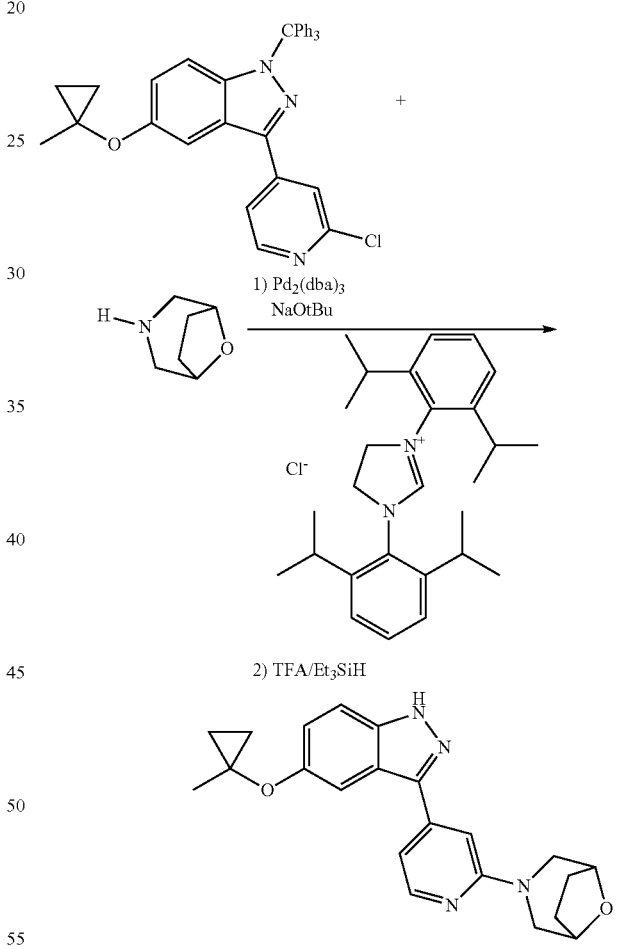

Example 4

The chloro-pyridine (150 mg), 8-oxa-3-azabicyclo[3.2.1]octane (41 mg), 1,3-bis(2,6-diisopropylphenyl)-4,5-dihydro-1H-imidazol-3-ium chloride (36 mg), Pd$_2$(dba)$_3$ (50 mg), and NaO$^t$Bu (53 mg) were taken up in 2 ml of dioxane in a sealed tube. The solution was heated at 100° C. for 24 h. The solution was filtered and concentrated. The residue was treated with 2 ml of TFA and 0.5 ml of Et$_3$SiH. After stirring at RT for 2 h, the solution was concentrated. The residue was treated with 5 ml of 7 NH$_3$ in MeOH, and the resulting solution was concentrated. The residue was purified via thin-layer preparative chromatography (40% EtOAc in hexanes, SiO$_2$) which provided Example 4 as a yellow solid.
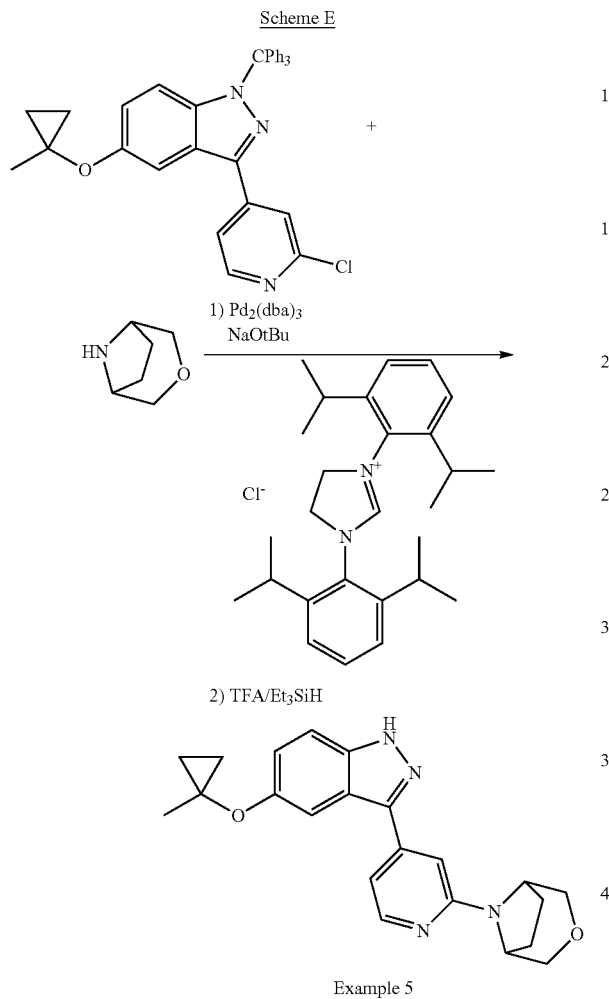
Example 5
The chloro-pyridine was reacted with 3-oxa-8-azabicyclo[3.2.1]octane using conditions outlined in Step 10 of Scheme D to provide Example 5.
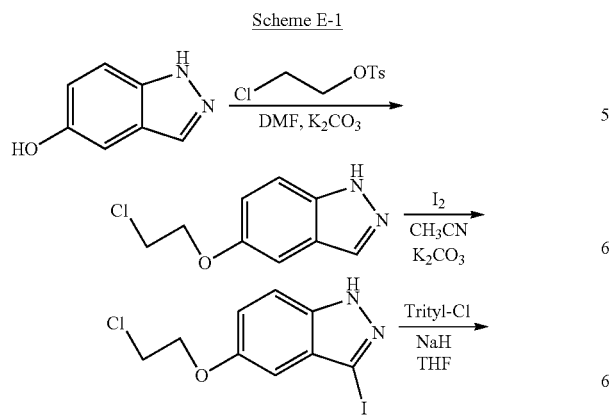
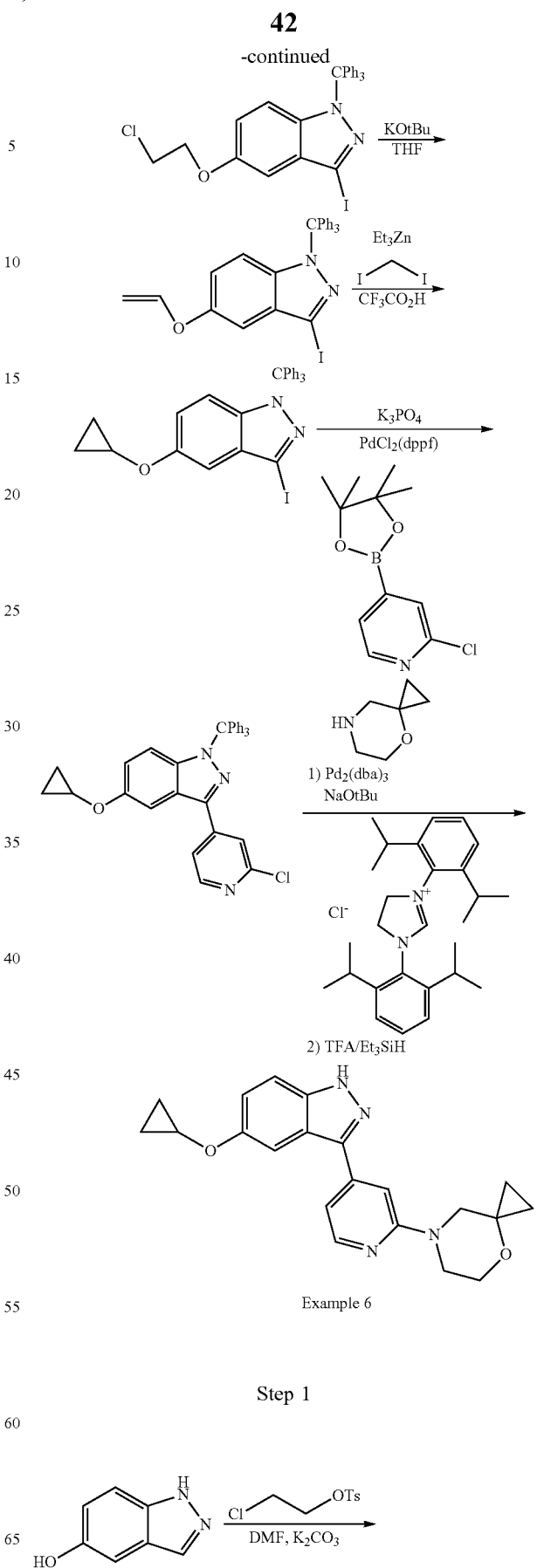
Example 6
Step 1

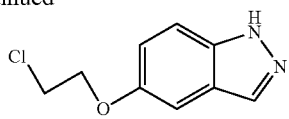

The hydroxyl-indazole (30 g) was taken up in DMF (200 ml). Potassium carbonate (62 g) was added to the solution, and the resulting mixture was stirred at RT for 15 minutes. 2-Chloroethyl-para-toluenesulfonate (43 ml) was added, and the resulting solution was heated at 50° C. for 20 h. The mixture was poured into water (600 ml) and quenched with acetic acid (26 ml). The mixture was filtered which provided a wet cake that was dried under reduced pressure. The brown solid was partitioned between EtOAc and water. The organic layer was dried (MgSO$_4$), filtered, and concentrated. After slurry of the residue in MTBE, the mixture was filtered which provided the desired product.

Step 2

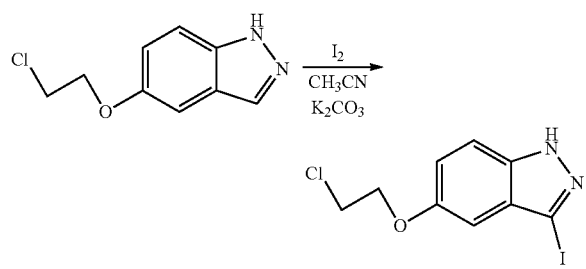

The chloro-indazole (36 g) was taken up in CH$_3$CN (500 ml). Potassium carbonate (24 g) and iodine (3 g) were added, and the resulting solution was stirred at RT for 1 h. The mixture was poured into water (1 L), and extracted with MTBE. The organic layer was washed with 10% Na$_2$S$_2$O$_3$ $_{(aq.)}$ and dried over MgSO$_4$. The solution was filtered and concentrated. The residue was adsorbed onto SiO$_2$ (90 g) and purified on a short pad of SiO$_2$ using a gradient elution of 10-30% EtOAc in hexanes. The solution was concentrated which provided the desired iodide.

Step 3

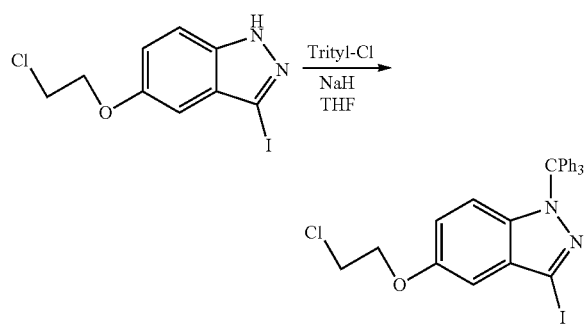

The indazole (17 g) was taken up in THF (100 ml) at 0° C. Sodium hydride (2.0 g) was added to the solution. After stirring at 0° C. for 10 minutes, trityl chloride (13.7 g) was added. The solution was warmed to RT for 2 hours. The solution was quenched with sat. NH$_4$Cl (aq.) and extracted with Et$_2$O. The aqueous layer was extracted with Et$_2$O. The combined organic layers were washed with brine and dried over MgSO$_4$. Filtration and concentration provided the crude product. The residue was slurried in hot MTBE. The solid was collected and dried. The solid was purified via gradient flash chromatography (0-10% MTBE in hexanes, SiO$_2$) which provided the trityl protected indazole.

Step 4

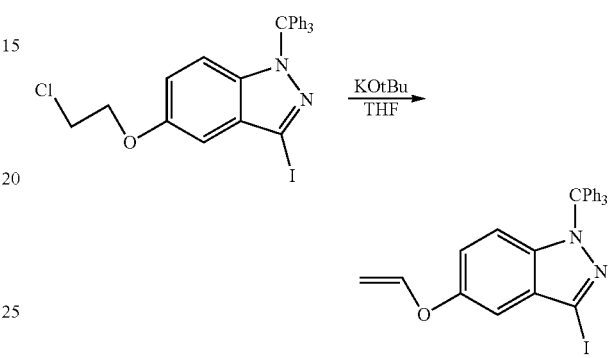

The chloro-indazole (20 g) was suspended in THF (120 mL), and potassium tert-butoxide (8.0 g) was added. After stirring at 2 hours at RT, the solution was partitioned between sat. NH$_4$Cl$_{(aq.)}$ and Et$_2$O. The aqueous layer was extracted with Et$_2$O. The combined organic layers were dried over MgSO$_4$. Filtration and concentration provided the desired alkene.

Step 5

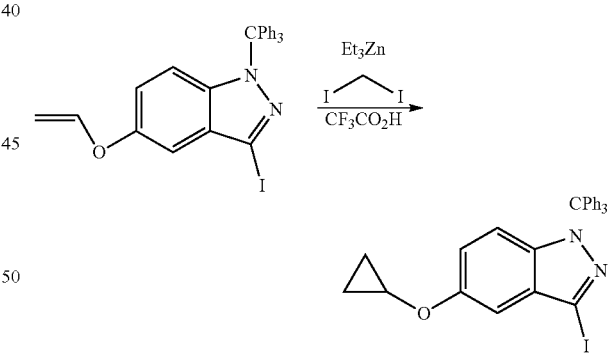

Diethyl zinc (57 ml of a 1.0M solution in hexane) and 20 ml of DCE were placed into a dry flask under nitrogen at RT. The solution was cooled to 0° C., and TFA (4.2 ml) in DCE (20 ml) was added over 30 minutes (exotherm/gas evolution). The white suspension was stirred at 0° C. for 15 minutes. Diiodomethane (4.6 ml) in DCE (20 ml) was added over 15 minutes at 0° C. The alkene (15.7 g) in DCE (100 ml) was added to the solution at 0° C. The solution was warmed to RT. After stirring at RT for 5 h, the solution was quenched with sat. NH$_4$Cl$_{(aq.)}$ and DCM. The aqueous layer was extracted with DCM. The combined organic layers were dried over MgSO$_4$. Filtration and concentration provided the crude product. The residue was purified via gradient flash chromatography (0-10% MTBE in hexanes, SiO$_2$) which provided the cyclopropoxy indazole.

Step 6

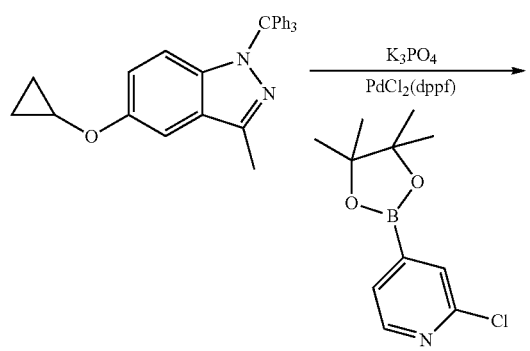

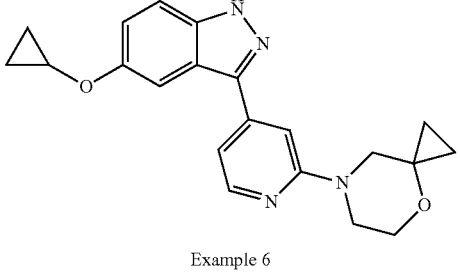

Example 6

The chloro-pyridine was reacted with 4-oxa-7-azaspiro[2.5]octane using conditions outlined in Step 10 of Scheme D to provide Example 6.

Scheme F

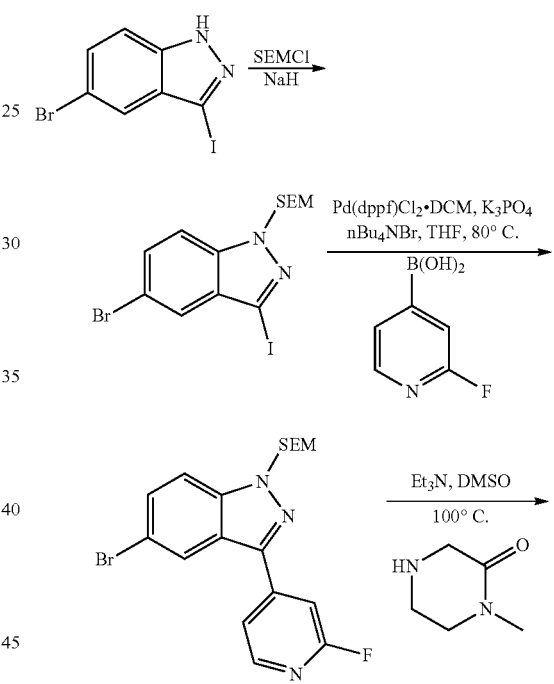

The indazole (1.4 g), boronate ester (742 mg), K$_3$PO$_4$ (3.8 ml of a 2 M aqueous solution), and PdCl$_2$(dppf)-DCM complex (211 mg) were taken up in 20 ml of DME. Argon was bubbled through the solution, and the mixture was placed into a sealed tube. The reaction was subjected to microwave irradiation (2 hours at 90° C.). The solution was cooled, filtered, and concentrated. The residue was purified by gradient flash chromatography (0-20% EtOAc in hexanes, SiO$_2$) which provided the chloro-pyridine.

Step 7

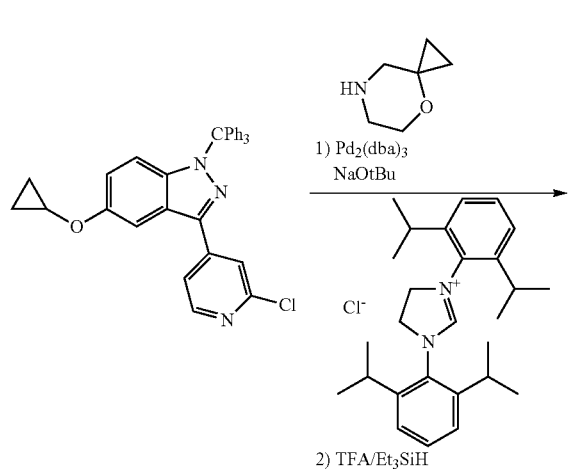

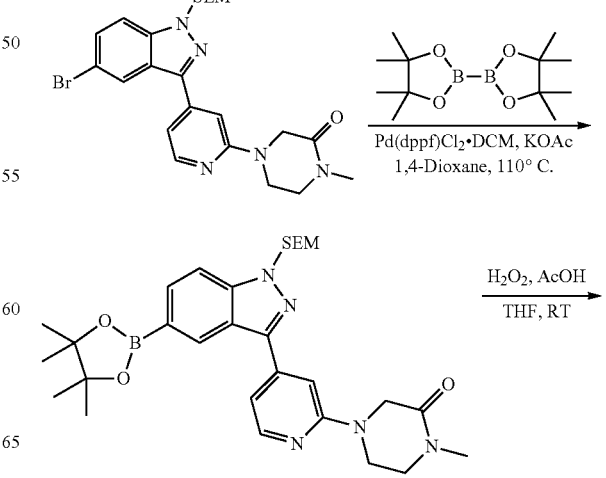

-continued

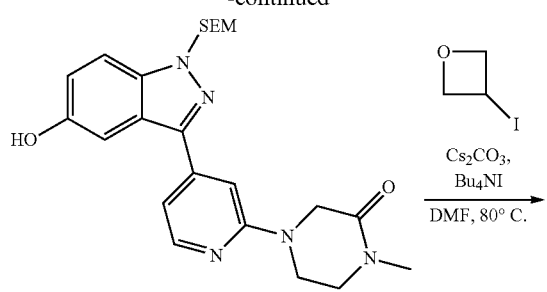

Step 2

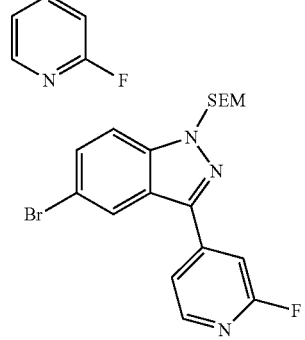

The iodo-indazole (1.6 g), boronic acid (497 mg), K₃PO₄ (2.2 g), and nBu₄NBr (228 mg) were taken up in THF (32 ml). Nitrogen was bubbled through the solution for 15 minutes, and Pd(dppf) Cl₂ DCM complex (577 mg) was added. The resulting solution was heated at 80° C. for 48 hours. The mixture was filtered though a plug of celite. The filtrate was concentrated, and then it was partitioned between EtOAc and water. The aqueous layer was extracted with EtOAc. The combined organic layers were dried over MgSO₄. Filtration and concentration provided the crude product. The residue was purified by gradient column chromatography (100/0 to 15/1 hexanes/EtOAc, SiO₂) to afford the arylated indazole.

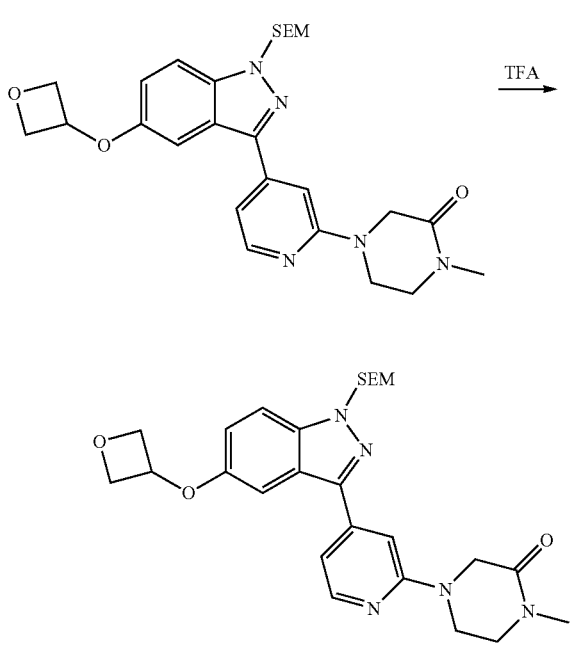

Example 7

Step 3

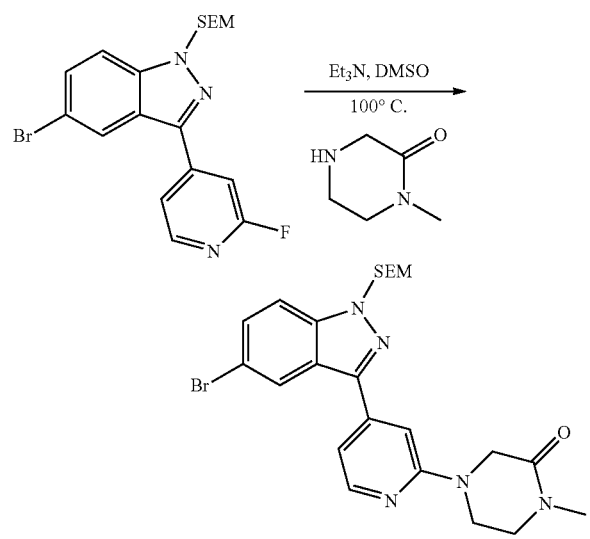

Step 1

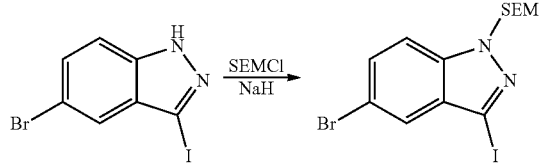

The indazole (2.2 g) was taken up in THF (25 ml) at 0° C. Sodium hydride (275 mg of a 60 wt % dispersion in oil) was added in portions. After stirring at 0° C. for 15 minutes, SEMCl (1.1 g) was added. The solution was warmed to RT. After stirring at RT for 20 hours, the reaction was partitioned between EtOAc and sat. NH4Cl$_{(aq.)}$. The aqueous layer was extracted with EtOAc. The combined organic layers were dried over MgSO₄. Filtration and concentration provided the crude product. The residue was purified by gradient flash chromatography (100/1 to 15/1 hexanes/EtOAc, SiO₂) to afford the desired SEM protected indazole.

The indazole (810 mg), Et₃N (3.9 g), and amine (1.9 g) were taken up in DMSO (4 ml). The resulting solution was heated in a sealed tube at 100° C. for 16 hours. The solution was cooled, and it was partitioned between EtOAc and water. The aqueous layer was extracted with EtOAc. The combined organic layers were dried (MgSO$_4$), filtered, and concentrated. The residue was purified by flash chromatography (30/1 DCM/MeOH, SiO$_2$) which provided the aminopyridine.

Step 4

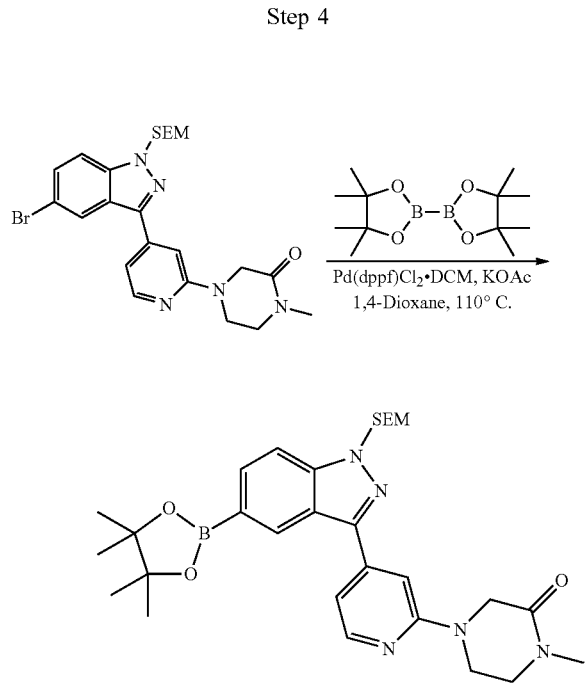

The bromo-indazole was converted into the boronate ester using conditions similar to those outlined in Step 4 of Scheme A.

Step 5

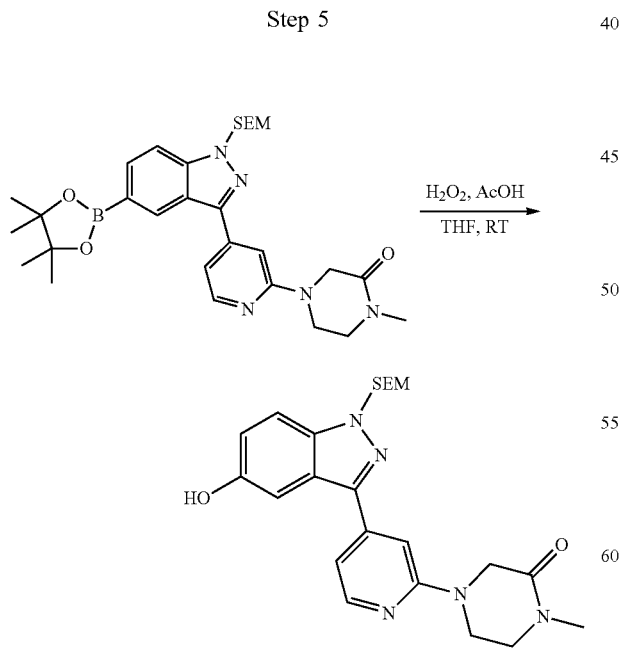

The boronate-ester was converted into the phenol using conditions similar to those outlined in Step 5 of Scheme A.

Step 6

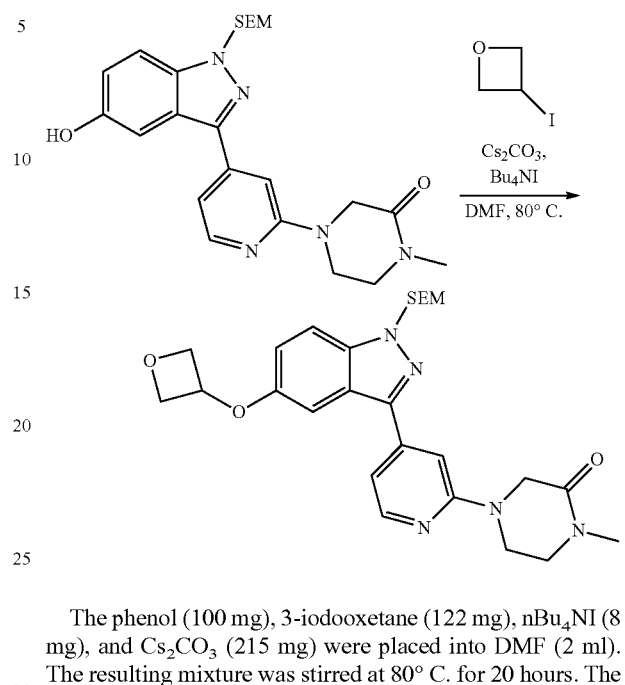

The phenol (100 mg), 3-iodooxetane (122 mg), nBu$_4$NI (8 mg), and Cs$_2$CO$_3$ (215 mg) were placed into DMF (2 ml). The resulting mixture was stirred at 80° C. for 20 hours. The mixture was filtered and concentrated. The residue was partitioned between EtOAc and water. The aqueous layer was extracted with EtOAc. The combined organic layers were dried (MgSO$_4$), filtered, and concentrated. The residue was purified by flash chromatography (30/1 DCM/MeOH, SiO$_2$) which provided the desired ether.

Step 7

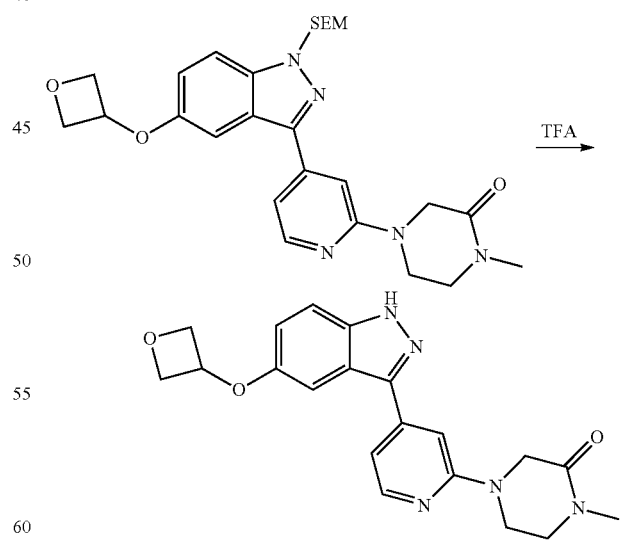

Example 7

The SEM protected indazole (69 mg) was taken up in 2 ml of DCM, and TFA (1 ml) was added. The solution was stirred at RT for 5 hours. The mixture was concentrated, and the residue was taken up in DCM (2 ml), MeOH (2 ml), and 1 M NH₄OH (2 ml). The mixture was stirred at RT for 20 hours. The mixture was diluted with water and extracted with DCM. The combined organic layers were dried (MgSO₄), filtered, and concentrated. The residue was purified by reverse phase chromatography to afford Example 7.

Scheme G

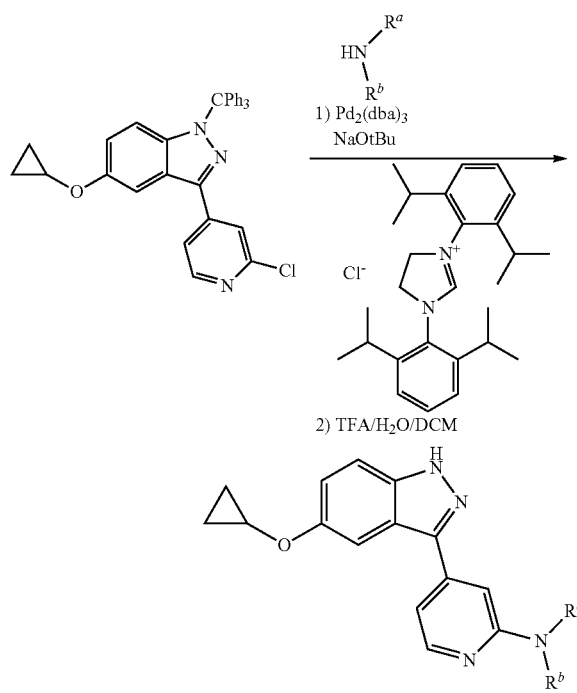

Example 8-26

Parallel preparation of Examples 8-26: To a set of vials each containing the requisite amine (0.152 mmol) if a solid, was added 1,3-Bis-(2,6-diisopropylphenyl)imidazolinium chloride (6.47 mg, 0.015 mmol), Pd₂(dba)₃ (3.47 mg, 3.79 μmol) and sodium t-butoxide (29.1 mg, 0.303 mmol). The vials were transferred to a glove bag under an atmosphere of N₂. A solution of the chloropyridine (Scheme E-1) (40 mg, 0.076 mmol) in dioxane (0.500 ml) was then added to each vial followed by the requisite amine (0.152 mmol) if it was a liquid. The vials were capped and removed from the glove bag. The vials were then placed into a pre-heated aluminium block at 90° C. The mixtures were stirred at that temperature overnight. Water (2 mL) was added to each vial followed by DCM (2.0 mL). The vials were shaken at RT for 5 min. The mixture was transferred to a fitted barrel filter. The organic layer from each vial was drained into a clean vial. Additional DCM (1 mL) was added to the aqueous layer and the layers were separated. The solvent from the combined organic layers was removed in vacuo. To each vial was then added DCM (1 mL) followed by TFA (0.50 mL) and water (0.050 mL). The vials were shaken at RT for 1.5 hours. The solvent was removed in vacuo. Each crude product was redissolved in 1 mL of DMSO and filtered. The crude products were purified by mass triggered HPLC. [Waters XBridge C18 column, 5 μm, 19×100 mm, gradient ranges from 10-30% initial to 30-70% MeCN (0.1% NH₄OH) in water (0.1% NH₄OH) 50 mL/min, 8 min run time] to provide the examples 8-25. Example 26 was repurified using the following conditions: [Waters Sunfire C18 column, 5 μm, 19×100 mm, gradient 10% initial to 30% final MeCN (0.1% formic acid) in water (0.1% formic acid) 50 mL/min, 8 min run time].

| Ex | Structure | LRRK2 IC$_{50}$ (nM) | Method | LCMS RT (min) | m/z |
|---|---|---|---|---|---|
| 1 | 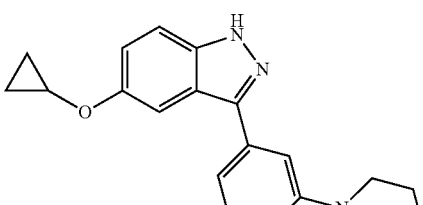 | 40 | A | 1.0 | 337 |
| 2 | 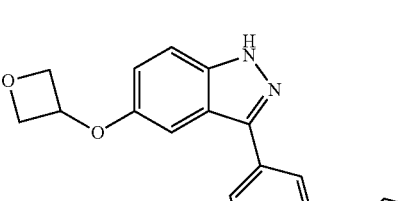 | 20 | B | 1.3 | 353 |

-continued

| | | LRRK2 | LCMS | | |
|---|---|---|---|---|---|
| Ex | Structure | IC$_{50}$ (nM) | Method | RT (min) | m/z |
| 3 | | 1.2 | B | 1.9 | 355 |
| 4 | | 23 | B | 2.0 | 377 |
| 5 | | 67 | B | 2.1 | 377 |
| 6 | | 17 | B | 2.1 | 363 |
| 7 | | 36 | B | 1.8 | 382 |

-continued

| Ex | Structure | LRRK2 IC₅₀ (nM) | LCMS Method | RT (min) | m/z |
|---|---|---|---|---|---|
| 8 | | 30 | C | 1.07 | 371.2 |
| 9 | | 16 | C | 0.91 | 307.2 |
| 10 | | 23 | C | 0.78 | 367.2 |
| 11 | | 111 | C | 0.80 | 411.2 |

|    |           | LRRK2 | LCMS | | |
|----|-----------|-------|------|---|---|
| Ex | Structure | IC₅₀ (nM) | Method | RT (min) | m/z |
| 12 | | 10 | C | 0.84 | 402.2 |
| 13 | | 16 | C | 0.97 | 401.2 |
| 14 | | 19 | C | 0.95 | 357.1 |
| 15 | | 44 | C | 0.77 | 383.2 |

US 9,688,654 B2
-continued
| Ex | Structure | LRRK2 IC$_{50}$ (nM) | LCMS Method | RT (min) | m/z |
|---|---|---|---|---|---|
| 16 | 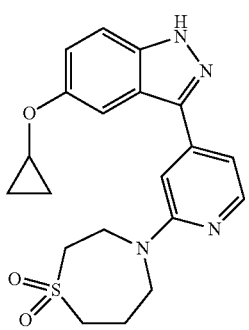 | 71 | C | 0.84 | 399.2 |
| 17 | 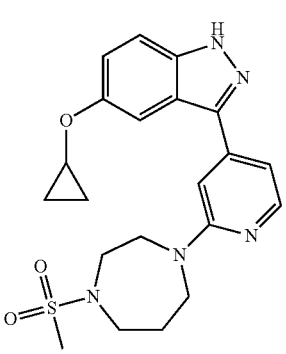 | 51 | C | 0.88 | 428.2 |
| 18 | 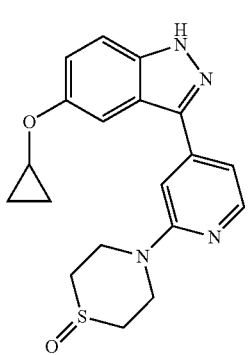 | 10 | C | 0.76 | 396.1 |
| 19 | 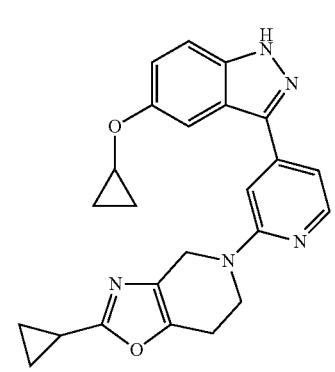 | 54 | C | 1.07 | 414.2 |

-continued
| Ex | Structure | LRRK2 IC$_{50}$ (nM) | LCMS Method | RT (min) | m/z |
|---|---|---|---|---|---|
| 20 | 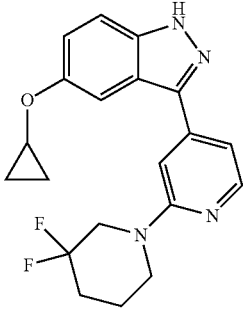 | 22 | C | 1.05 | 371.2 |
| 21 | 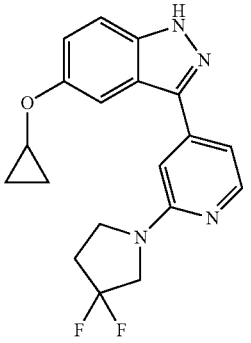 | 19 | C | 1.01 | 357.2 |
| 22 | 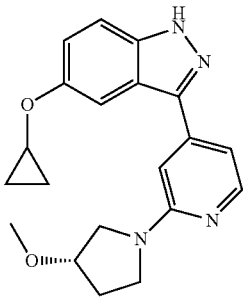 | 17 | C | 0.91 | 351.2 |
| 23 | 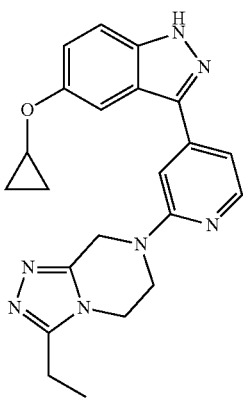 | 12 | C | 0.80 | 402.2 |

| Ex | Structure | LRRK2 IC$_{50}$ (nM) | LCMS Method | RT (min) | m/z |
|---|---|---|---|---|---|
| 24 | | 29 | C | 0.77 | 337.2 |
| 25 | | 40 | C | 0.97 | 343.1 |
| 26 | | 12 | C | 0.99 | 376.2 |
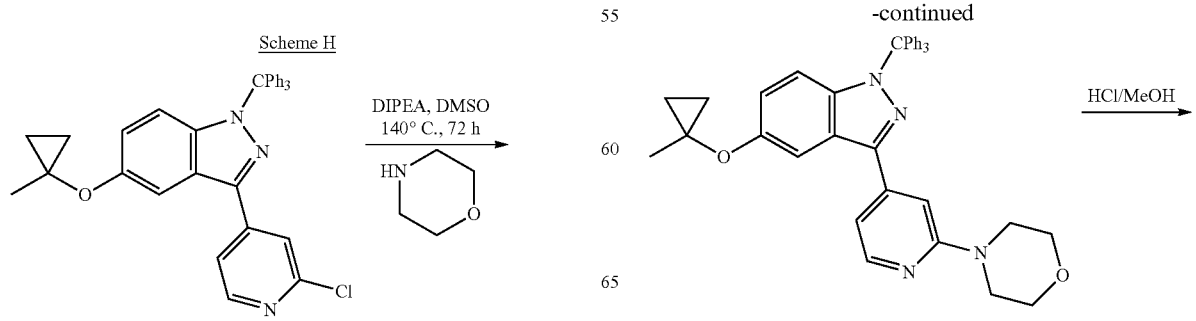
Scheme H

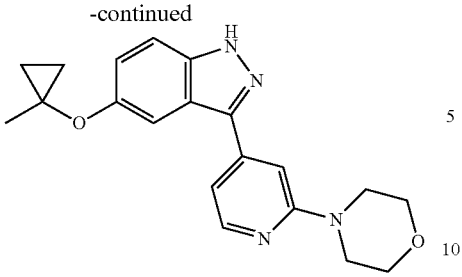

Example 27

Step 1

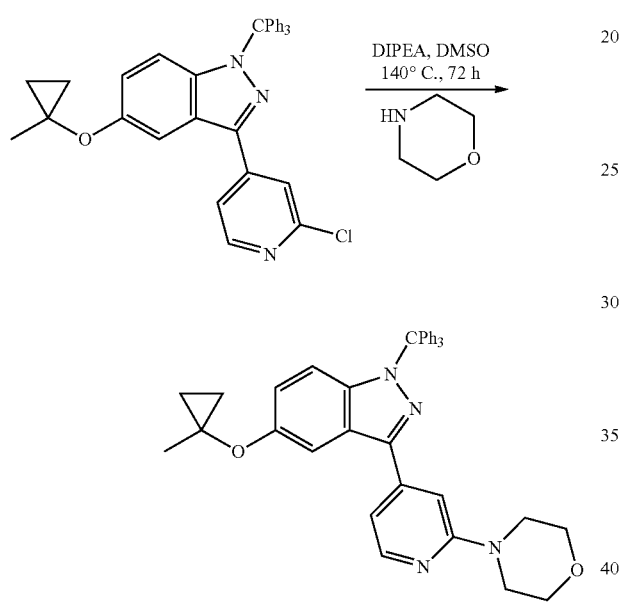

water (15 mL), and then extracted with EtOAc (30 mL×3). The combined organic layers were washed with water (45 mL), and brine (45 mL), dried over Na$_2$SO$_4$, filtered and concentrated to leave a residue which was purified by a silica gel chromatography column (elute: petroleum ether/EtOAc=10/1) to yield the desired product as a yellow solid. MS (ESI) m/z=593.1 [M+1]$^+$.

Step 2

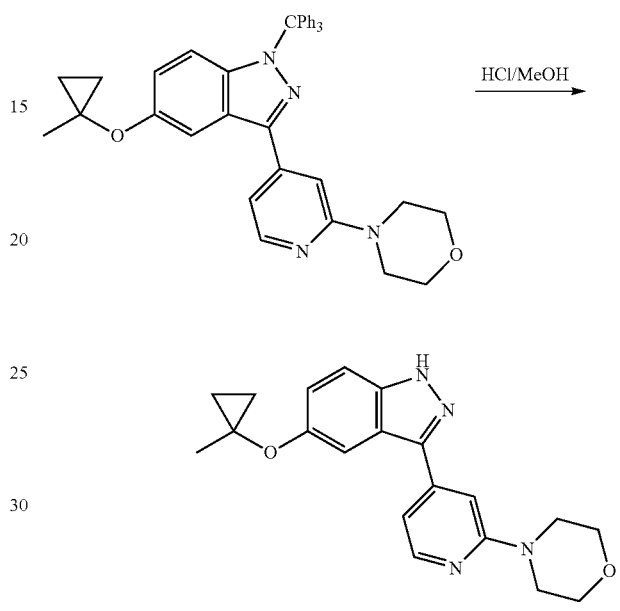

Example 27

The chloropyridine from Step 9 of Scheme D (150 mg, 0.27 mmol), morpholine, and N,N-diisopropylethylamine (208 mg, 1.62 mmol) were taken up into DMSO (4 mL). The reaction was sealed and heated at 140° C. for 72 h. The mixture was cooled to room temperature and diluted with The trityl protected indazole from the previous step (110 mg, 0.18 mmol) in methanol (4 mL) was added a solution of hydrogen chloride in methanol (3.0 M, 1.0 mL, 3.0 mmol). The mixture was heated at 70° C. for 6 h. The reaction was cooled, and then concentrated to leave a residue, which was purified by a silica gel chromatography column (elute: EtOAc/MeOH=10/1) to yield the desired product as a white solid. MS (ESI) m/z=351.1 [M+1]$^+$; RT=1.6 minutes (LCMS conditions D).

The following examples (28-37) were prepared in a similar fashion to that depicted in Scheme H using the appropriate amine.

| Ex | Structure | LRRK2 IC$_{50}$ (nM) | LCMS Method | RT (min) | m/z |
|---|---|---|---|---|---|
| 27 | 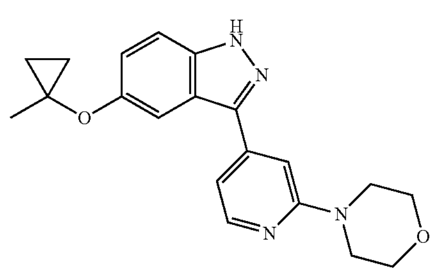 | 0.6 | D | 1.6 | 351.1 |

-continued
| Ex | Structure | LRRK2 IC$_{50}$ (nM) | LCMS Method | RT (min) | m/z |
|---|---|---|---|---|---|
| 28 | 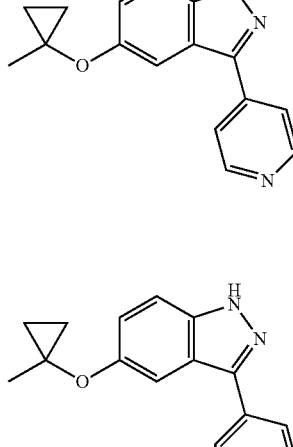 | 0.6 | D | 1.7 | 365.1 |
| 29 | 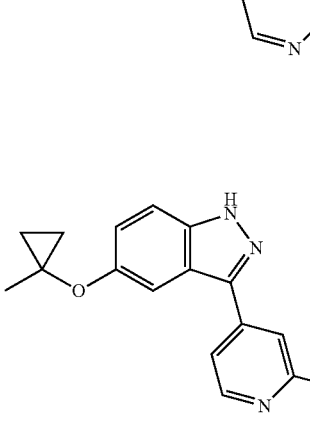 | 0.6 | D | 1.7 | 365.1 |
| 30 | 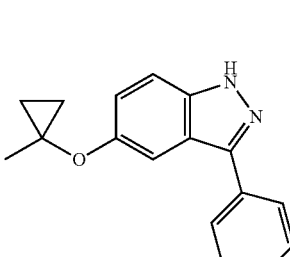 | 0.9 | D | 1.7 | 379.2 |
| 31 |  | 0.6 | D | 1.7 | 428.1 |
| 32 | | 0.6 | D | 1.6 | 364.1 |

-continued

| Ex | Structure | LRRK2 IC$_{50}$ (nM) | LCMS Method | RT (min) | m/z |
|---|---|---|---|---|---|
| 33 | | 1.0 | D | 1.7 | 378.1 |
| 34 | | 0.7 | D | 1.6 | 381.1 |
| 35[a] | | 1.1 | D | 1.6 | 380.2 |
| 36[b] | | 2.0 | D | 1.6 | 350.0 |
| 37[b] | | 2.6 | D | 1.5 | 350.0 |

[a] The preparation of the requisite Boc protected amine for Example 35 is shown in Scheme I.
The Boc group is cleaved in Step 2 of Method D.

Scheme I

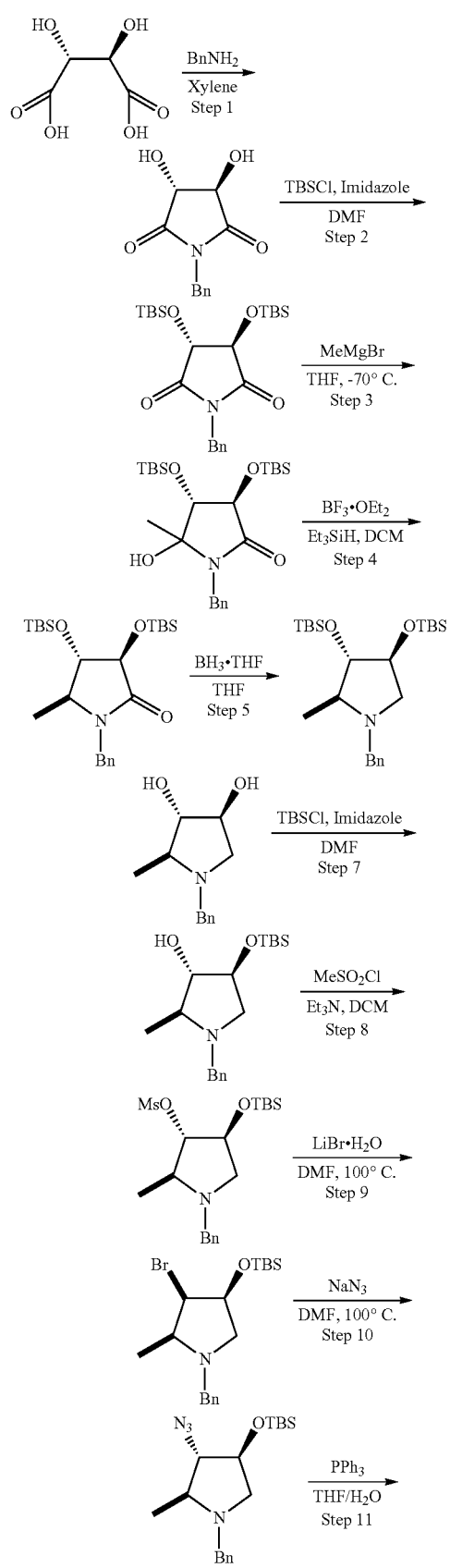

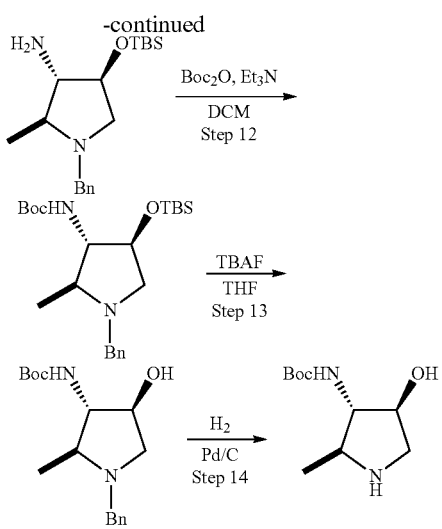

Step 1:

A mixture of L-tartaric acid (250 g, 1.67 mol) and BnNH$_2$ (178 g, 1.67 mol) in xylene (1.5 L) was stirred under reflux for 4 h using a Dean-Stark water separator. The reaction was cooled to room temperature with stirring and filtrated. The solid was washed with EtOH to afford the desired product as a yellow solid.

Step 2:

To a stirred solution of diol from Step 1 (275 g, 1.24 mol) in DMF (1.8 L) was added imidazole (254 g, 3.73 mol) followed by TBSCl (467 g, 3.11 mol). The reaction mixture was stirred at rt overnight before being diluted with EtOAc. The resulting layer was washed with water and brine, dried, filtered and concentrated to leave a residue which was purified by column chromatography on silica gel (elution with petroleum ether:EtOAc 100:1) to afford the desired product as a colorless oil.

Step 3:

To a cold (−70° C.), stirred solution of compound from Step 2 (270 g, 0.6 mol) in THF (3 L) was added MeMgBr (400 ml of 1.0 M solution in THF, 1.2 mol) dropwise. The reaction mixture was slowly warmed to −10° C. and then to rt before being quenched with a saturated aqueous solution of NH$_4$Cl. The organic layer was separated and the aqueous layer was extracted with EtOAc. The combined organic layers were dried, filtered and concentrated under reduced pressure to leave a residue which and purified by column chromatography on silica gel (elution with 50:1 to 10:1 petroleum ether:EtOAc) to afford the desired product as a white solid.

Step 4:

To a cold (−70° C.), stirred solution of compound from Step 3 (350 g, 0.75 mol) in DCM (2 L) was added Et$_3$SiH (870 g, 7.5 mol) followed by a solution of BF$_3$.Et$_2$O (139 ml, 1.125 mol) dropwise. The reaction mixture was warmed up to rt before being quenched with a saturated aqueous solution of NaHCO$_3$. The organic layer was separated and the aqueous layer was extracted with DCM. The combined organic layers were dried, filtered and concentrated under reduced pressure to leave a residue which and purified by column chromatography on silica gel (elution with petroleum ether:EtOAc 10:1) to afford the desired product as a colorless oil.

Step 5:
A mixture of compound from Step 4 (325 g, 0.72 mol) and BH$_3$.THF (1800 mL of 1.0 M solution in THF, 1.8 mol) in THF (500 mL) was stirred at reflux for 6 h. The reaction was cooled and EtOH (300 ml) was added dropwise. The mixture was stirred at reflux for additional 2 h followed by cooling to rt. The reaction mixture was concentrated to leave a residue which was dissolved in DCM. The organic layer was washed with a saturated aqueous solution of NaHCO$_3$, dried, filtered and concentrated to afford the desired product as a yellow oil.

Step 6:
To a stirred solution of compound from Step 5 (438 g, 1.0 mol) in THF (2.5 L) was added TBAF (657 g, 2.5 mol) and the resulting mixture was stirred at rt overnight. The reaction mixture concentrated under reduced pressure to leave a residue which was directly purified by column chromatography on silica gel (elution with 1:1 to 0:100 petroleum ether:EtOAc) to afford the diol as a white solid.

Step 7:
To a solution of diol from Step 6 (95 g, 0.46 mol) in DMF (1 L) was added imidazole (47 g, 0.69 mol) followed by TBSCl (76 g, 0.5 mol). The reaction was stirred at rt overnight. The reaction was diluted with EtOAc and the resulting layer was washed with water and brine, dried, filtered and concentrated under reduced pressure to leave a residue which was purified by column chromatography on silica gel (elution with 4:1 petroleum ether:EtOAc) to afford the desired product as a yellow oil.

Step 8:
To a cold (0° C.), stirred solution of alcohol from Step 7 (75 g, 0.234 mol) in DCM (750 mL) was added Et$_3$N (49 ml, 0.35 mol) followed by MeSO$_2$Cl (32 g, 0.28 mol) dropwise. The resulting mixture was stirred at 0° C. for 2 h. The mixture was washed with water and brine, dried, filtered and concentrated to afford the desired mesylate as a brown oil which was directly used in the next step without further purification.

Step 9:
A mixture of mesylate from Step 8 (93 g, 0.233 mol) and LiBr.H$_2$O (245 g, 2.33 mol) in DMF (1 L) was stirred at 100° C. overnight. After being cooled to room temperature the reaction was diluted with EtOAc. The resulting layer was washed with water and brine, dried, filtered and concentrated under reduced pressure to leave a residue which was purified by column chromatography on silica gel (elution with 50:1 petroleum ether:EtOAc) to afford the desired product as a colorless oil.

Step 10:
A mixture of bromide from Step 9 (64 g, 0.167 mol) and NaN$_3$ (33 g, 0.5 mol) in DMF (600 mL) and water (50 mL) was stirred at 100° C. for 2 days. After being cooled to room temperature the reaction was diluted with EtOAc, washed with water and brine, dried, filtered and concentrated to leave a brown oil which was directly used in the next step without further purification.

Step 11:
A mixture of azide from Step 10 (0.344 mol) and PPh$_3$ (262 g, 1.0 mol) in THF (1.5 L) and water (150 mL) was stirred at 90° C. for 2 h. The reaction was concentrated under reduced pressure to leave a residue which was diluted with water (500 ml) followed by the addition of 6N HCl until pH 1-2. The aqueous layer was extracted with EtOAc. The aqueous phase was adjusted to pH 9-10 by adding an aqueous solution of NaOH (10%). The resulting layer was extracted with DCM. The organic layer was washed with brine, dried, filtered and concentrated under reduced pressure to afford the desired amine as a brown oil.

Step 12:
To a stirred solution of amine from Step 11 (156 g, 0.49 mol) in DCM (2 L) was added Et$_3$N (103 ml, 0.73 mol) followed by Boc$_2$O (128 g, 0.59 mol). After being stirred at rt for 2 h the reaction was washed with water and brine, dried, filtered and concentrated under reduced pressure to leave a residue which was purified by column chromatography on silica gel (elution with 20:1 petroleum ether: EtOAc) to afford the desired product as a white solid.

Step 13:
To a stirred solution of compound from Step 12 (60 g, 0.143 mol) in THF (1 L) was added TBAF (56 g, 0.214 mol) and the resulting mixture was stirred at room temperature overnight. The mixture was concentrated and the residue was purified by column chromatography on silica gel (elution with 1:1 to 1:5 Petroleum ether:EtOAc) to afford the desired product as a white solid.

Step 14:
To a stirred solution of compound from Step 13 (39 g, 0.127 mol) in MeOH (800 mL) was added 10% wet Pd/C (4 g). The flask was evacuated and back-filled with H$_2$ (×2). The resulting mixture was then stirred at 30° C. for 24 h. The reaction was filtrated and the filtrate was concentrated to obtain the desired amine as a gray solid.

$^a$The amines used to prepare Examples 36 and 37 are shown below. The Boc group was cleaved during step 2.

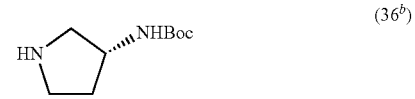

(36$^b$)

(37$^b$)

LCMS Methods
A—Mobile Phase: A: water (0.1% TFA): B: ACN (0.1% TFA); Gradient: 90:10 to 2:98 (A:B) over 1.5 min, 2:98 (A:B) for 1.5 min; Flow rate: 1.5 ml/min; Column: Waters Extera (2.1×20 mm)
B—Mobile Phase: A: water (0.05% TFA): B: ACN (0.05% TFA); Gradient: 90:10 to 5:95 (A:B) over 1.2 min, 5:95 (A:B) for 1.2 min; Flow rate: 1.0 ml/min; Column: Agilent Zorbax SB-C18 (3.0×50 mm)
C—Gradient 5:95 to 100:0 MeCN (0.1% NH$_4$OH): water (0.1% NH$_4$OH) over 1.4 min; Waters Acquity UPLC, column: Waters BEH-C18, 1.7 um, 2.1×50 mm 1 mL/min flow
D—Mobile Phase: A: water (0.01% TFA) B: ACN (0.01% TFA); Gradient: 5%-95% B in 1.5 min; Flow Rate: 1.8 ml/min; Column: Sunfire C18, 4.6×50 mm Biological Assays
The data presented for the 5 mM and Km ATP LanthaScreen™ Assay represents mean IC$_{50}$ values based on several test results and may have reasonable. deviations depending on the specific conditions and reagents used. Reagents for the LRRK2 5 mM and Km ATP LanthaScreen™ Assay were purchased from Life Technologies Corporation.

LRRK2 5 mM ATP LanthaScreen™ Assay
a) 400 nl of a 1:2.15 serial dilution of test compound (98 μM top assay concentration) is spotted via Labcyte Echo to certain wells in a 384 well black, untreated plate. Control wells contain 400 nl of either DMSO or 400 nl of a known inhibitor in DMSO.

b) 10 μl of a 2.5 nM LRRK2 (G2019S mutation, GST-LRRK2 (amino acids 970-2527)) enzyme solution in 1× assay buffer (50 mM Tris pH 8.5, 10 mM MgCl$_2$, 0.01% Brij-35, 1.0 mM EGTA, 2 mM DTT, 0.05 mM NaVO$_4$) is added to all wells.

c) A 30 minute room temperature incubation is followed by addition of 10 μl of 800 nM fluorescein labeled LRRKtide peptide substrate and 10 mM ATP solution in 1× assay buffer to all wells.

d) After a 35 minute room temperature incubation, 20 μl of TR-FRET Dilution Buffer (Invitrogen PV3756B) containing 4 nM Tb-labeled anti-phospho LRRKtide antibody and 20 mM EDTA is added to all wells.

e) Plates are incubated at room temperature for 1 hour and read on an Envision™ multi-mode plate reader with LanthaScreen™ settings. Results are analysed using Assay Data Analyzer.

LRRK2 Km ATP LanthaScreen™ Assay a) 400 nl of a 1:2.15 serial dilution of test compound (98 μM top assay concentration) is spotted via Labcyte Echo to certain wells in a 384 well black, untreated plate. Control wells contain 400 nl of either DMSO or 400 nl of a known inhibitor in DMSO.

b) 10 μl of a 2.5 nM LRRK2 (G2019S mutation, GST-LRRK2 (amino acids 970-2527)) enzyme solution in 1× assay buffer (50 mM Tris pH 8.5, 10 mM MgCl$_2$, 0.01% Brij-35, 1 mM EGTA, 2 mM DTT, 0.05 mM NaVO$_4$) is added to all wells.

c) A 30 minute room temperature incubation is followed by addition of 10 μl of 800 nM fluorescein labeled LRRKtide peptide substrate and 186 μM ATP solution in 1× assay buffer to all wells.

d) After a 60 minute room temperature incubation, 20 μl of TR-FRET Dilution Buffer (Invitrogen PV3756B) containing 4 nM Tb-labeled anti-phospho LRRKtide antibody and 20 mM EDTA is added to all wells.

e) Plates are incubated at room temperature for 1 hour and read on an Envision™ multi-mode plate reader with LanthaScreen™ settings. Results are analysed using Assay Data Analyzer.

TABLE A 5 mM ATP LanthaScreen ™ Assay Data of representative compounds
In the table below, representative examples are provided with their respective IC$_{50}$ in the 5 mM ATP LanthaScreen ™ Assay. Preferred compounds have an IC$_{50}$ less than 1 μM in the 5 mM ATP LanthaScreen Assay.

| Example | IC$_{50}$ (nM) |
|---|---|
| 9 | 225 |
| 23 | 297 |
| 26 | 300 |

TABLE B

Kinase selectivity of representative compounds
Kinase selectivity was performed using Z'-LYTE ™ or Adapta ® assay platforms available from Life Technologies Corporation. Values in Table B are percent inhibition in the presence of 1 micromolar of the indicated example.

| Kinase | Assay Platform | Ex. 29 | Ex. 28 | Ex. 30 | Ex. 27 |
|---|---|---|---|---|---|
| AURKB (Aurora B) | A | 11 | 11 | 6 | 15 |
| BRAF V599E | A | 18 | 19 | 5 | 29 |
| CDK1/cyclin B | A | 26 | 25 | 9 | 33 |

TABLE B-continued

Kinase selectivity of representative compounds
Kinase selectivity was performed using Z'-LYTE ™ or Adapta ® assay platforms available from Life Technologies Corporation. Values in Table B are percent inhibition in the presence of 1 micromolar of the indicated example.

| Kinase | Assay Platform | Ex. 29 | Ex. 28 | Ex. 30 | Ex. 27 |
|---|---|---|---|---|---|
| CHEK2 (CHK2) | A | 2 | 4 | 8 | 14 |
| CLK2 | A | 53 | 42 | 49 | 46 |
| DYRK1A | A | 4 | 2 | 3 | 6 |
| IRAK1 | B | 8 | −5 | −17 | 18 |
| JAK3 | A | 46 | 49 | 37 | 56 |
| MAPK1 (ERK2) | A | 18 | 23 | 10 | 23 |
| MAPK8 (JNK1) | A | 54 | 58 | 39 | 61 |

A—Z-LYTE ™;
B—Adapta ®

The invention claimed is:
1. A compound of the formula:

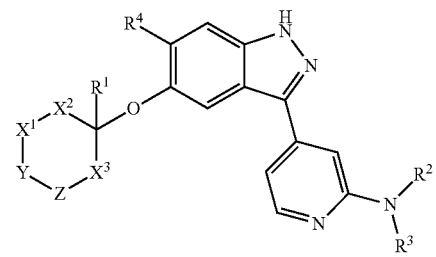

wherein X$^1$, X$^2$ and X$^3$ are each independently selected from the group consisting of a bond or CR$^e$R$^f$;
Y is O, CR$^a$R$^b$ or NR$^c$;
Z is O, CR$^a$R$^b$ or NR$^c$;
R$^1$ is selected from the group consisting of hydrogen and C$_{1-6}$ alkyl, which is optionally substituted with one to three substituents independently selected from the group consisting of halo, cyano, hydroxyl, NR$^c$R$^d$, OR$^5$ and (C=O)OR$^5$;
R$^2$ is selected from the group consisting of hydrogen and C$_{1-6}$ alkyl, which is optionally substituted with one to three substituents independently selected from the group consisting of:
 a) halo,
 b) cyano,
 c) R$^5$,
 d) R$^7$,
 e) OR$^5$, and
 f) NR$^c$R$^d$;
R$^3$ is selected from the group consisting of:
 a) hydrogen,
 b) C$_{1-6}$ alkyl, which is optionally substituted with one to three substituents independently selected from the group consisting of halo, cyano, OR$^5$ and NR$^c$R$^d$,
 c) C$_{3-8}$ cycloalkyl, which is optionally substituted with one to three substituents independently selected from the group consisting of halo, cyano, OR$^5$ and NR$^c$R$^d$,
 d) heterocyclyl, which is optionally substituted with one to three substituents independently selected from the group consisting of halo, cyano, oxo, R$^5$, OR$^5$ and NR$^c$R$^d$,
 e) heteroaryl, which is optionally substituted with one to three substituents independently selected from the group consisting of halo, cyano, oxo, R$^5$, OR$^5$ and NR$^c$R$^d$;

f) $C_{4-8}$ cycloalkenyl, which is optionally substituted with one to three substitutents independently selected from the group consisting of halo, cyano, $OR^5$ and $NR^cR^d$,
g) $(C=O)R^7$,
h) $(C=O)R^5$,
i) $S(O)_mR^5$, and
j) $S(O)_mR^7$;

or $R^2$ and $R^3$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
a) halo,
b) oxo,
c) cyano,
d) $OR^5$,
e) $NR^cR^d$,
f) $SO_3H$,
g) $S(O)_mR^5$,
h) $S(O)_mR^7$
i) $R^5$,
j) $R^6$,
k) $R^7$,
l) $(C=O)R^5$,
m) $(C=O)OR^5$,
n) $(C=O)R^7$, and
o) $(C=O)NR^cR^d$;

$R^4$ is selected from the group consisting of hydrogen, halo, cyano, $OR^5$, aryl, heteroaryl, $C_{3-8}$ cycloalkyl, $C_{4-8}$ cycloalkenyl, $C_{4-8}$ heterocycloalkyl and $C_{1-6}$ alkyl, which is optionally substituted with one to three substitutents independently selected from the group consisting of halo, cyano, $OC_{1-3}$ alkyl, $NR^cR^d$ and hydroxyl;

$R^5$ is selected from the group consisting of hydrogen and $C_{1-6}$ alkyl, which is optionally substituted with one to three substituents independently selected from the group consisting of:
a) halo,
b) hydroxyl,
c) $OC_{1-6}$ alkyl,
d) $NR^cR^d$,
e) $(C=O)NR^cR^d$,
f) $S(O)_m$,
g) $S(O)_mR^8$,
h) $S(O)_mR^7$,
i) $R^7$, and
j) $OR^7$;

$R^6$ is $C_{1-6}$ alkyl, which is optionally substituted with one to three substituents independently selected from the group consisting of halo and hydroxyl;

or $R^5$ and $R^6$ can be taken together with the atoms to which they are attached to form a 4 to 8 membered heterocyclic, 3 to 8 membered carbocyclic, aryl or heteroaryl ring, wherein said heterocyclic and heteroaryl rings may contain from one to three heteroatoms selected from N, O and S, wherein said heterocyclic, carbocyclic, aryl and heteroaryl rings are optionally substituted with one to three substituents independently selected from the group consisting of:
a) halo,
b) oxo,
c) cyano,
d) hydroxyl,
e) $C_{1-3}$ alkyl, which is optionally substituted with one to three halo,
f) $C_{3-8}$ cycloalkyl,
g) $OC_{1-3}$ alkyl, which is optionally substituted with one to three halo, and
h) $OC_{3-8}$ cycloalkyl;

$R^7$ is selected from the group consisting of $C_{4-8}$ heterocyclyl, $C_{3-8}$ cycloalkyl, $C_{4-8}$ cycloalkenyl, aryl or heteroaryl, wherein said heterocyclyl, cycloalkyl, cycloalkenyl, aryl and heteroaryl groups are optionally substituted with one to three substituents independently selected from the group consisting of:
a) halo,
b) cyano,
c) hydroxyl,
d) oxo,
e) $C_{1-3}$ alkyl, which is optionally substituted with one to four substituents independently selected from the group consisting of hydroxyl, halo, cyano, heterocyclyl, $OC_{1-3}$ alkyl and $NR^cR^d$,
f) $OC_{1-3}$ alkyl, which is optionally substituted with one to four substituents independently selected from the group consisting of hydroxyl, halo, cyano, heterocyclyl, $OC_{1-3}$ alkyl $NR^cR^d$ and aryl,
g) $C_{3-8}$ cycloalkyl, which is optionally substituted with one to four substituents independently selected from the group consisting of hydroxyl, halo, cyano, heterocyclyl, $OC_{1-3}$ alkyl and $NR^cR^d$,
h) aryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$,
i) heteroaryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$,
j) heterocyclyl, which is optionally substituted with one to four substituents independently selected from the group consisting of hydroxyl, halo, cyano, $OC_{1-3}$ alkyl and $NR^cR^d$,
k) $C_{4-8}$ cycloalkenyl, which is optionally substituted with one to four substituents independently selected from the group consisting of hydroxyl, halo, cyano, heterocyclyl, $OC_{1-3}$ alkyl and $NR^cR^d$;

$R^8$ is hydrogen or $C_{1-6}$ alkyl, which is optionally substituted with one to three substituents independently selected from the group consisting of:
a) halo,
b) cyano,
c) hydroxyl,
d) $OC_{1-3}$ alkyl, which is optionally substituted with one to four substituents independently selected from the group consisting of hydroxyl, and halo, and
e) $C_{3-8}$ cycloalkyl;

$R^a$ is selected from the group consisting of hydrogen and $C_{1-6}$ alkyl;

$R^b$ is selected from the group consisting of hydrogen and $C_{1-6}$ alkyl;

$R^c$ is selected from the group consisting of:
a) hydrogen and
b) $C_{1-3}$ alkyl, which is optionally substituted with one to three substituents independently selected from the group consisting of halo, hydroxyl, cyano, heteroaryl, aryl, $NH(C_{1-3}$ alkyl), $N(C_{1-3}$ alkyl)$_2$, $OC_{1-6}$ alkyl, and $C_{3-8}$ cycloalkyl;

$R^d$ is selected from the group consisting of:
a) hydrogen,
b) $C_{3-8}$ cycloalkyl,
c) $C_{3-6}$ heterocyclyl,
d) $C_{1-3}$ alkyl,
e) (C=O)$C_{1-3}$ alkyl,
f) aryl, and
g) heteroaryl;
wherein said cycloalkyl, heterocyclyl, alkyl, aryl and heteroaryl groups are each optionally substituted with one to three substituents independently selected from the group consisting of halo, hydroxyl, cyano, $R^8$, $SO_2R^8$, $OC_{1-6}$ alkyl and $C_{3-8}$ cycloalkyl,
or $R^c$ and $R^d$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of halo, cyano, hydroxyl, $C_{1-3}$ alkyl and $OC_{1-3}$ alkyl;
$R^e$ is selected from the group consisting of hydrogen and $C_{1-3}$ alkyl;
$R^f$ is selected from the group consisting of hydrogen and $C_{1-3}$ alkyl;
m is an integer from zero to two,
or a pharmaceutically acceptable salt thereof.

2. The compound of claim 1 wherein $X^1$, $X^2$ and $X^3$ are each a bond, or a pharmaceutically acceptable salt thereof.

3. The compound of claim 2 wherein Y is O or $CR^aR^b$ and Z is O or $CR^aR^b$; or a pharmaceutically acceptable salt thereof.

4. The compound of claim 3 wherein $R^1$ is selected from the group consisting of: hydrogen and $C_{1-3}$ alkyl, or a pharmaceutically acceptable salt thereof.

5. The compound of claim 4 wherein $R^4$ is selected from the group consisting of: hydrogen and halo, or a pharmaceutically acceptable salt thereof.

6. The compound of claim 5 wherein $R^2$ and $R^3$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
a) halo,
b) oxo,
c) cyano,
d) $OR^5$,
e) $NR^cR^d$,
f) $SO_3H$,
g) $S(O)_mR^5$,
h) $S(O)_mR^7$
i) $R^5$,
j) $R^6$,
k) $R^7$,
l) (C=O)$R^5$,
m) (C=O)$OR^5$,
n) (C=O)$R^7$, and
o) (C=O)$NR^cR^d$;
or a pharmaceutically acceptable salt thereof.

7. The compound of claim 6 wherein $R^2$ and $R^3$ can be taken together with the atoms to which they are attached to form a 6 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
a) halo,
b) oxo,
c) $OR^5$,
d) $NR^cR^d$,
e) $S(O)_mR^5$,
f) $S(O)_mR^7$,
g) $R^5$,
h) $R^6$,
i) $R^7$,
j) (C=O)$R^5$,
k) (C=O)$OR^5$, and
l) (C=O)$R^7$;
or a pharmaceutically acceptable salt thereof.

8. A compound selected from

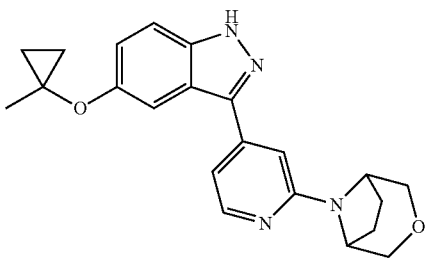

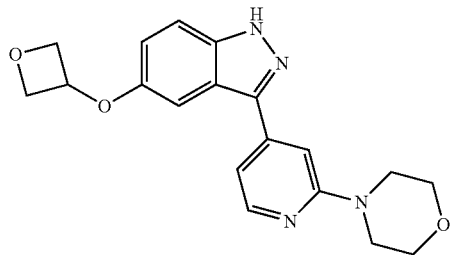 [SMILES: c1cc(-c2n[nH]c3ccc(OC4COC4)cc23)cc(N2CCOCC2)n1]

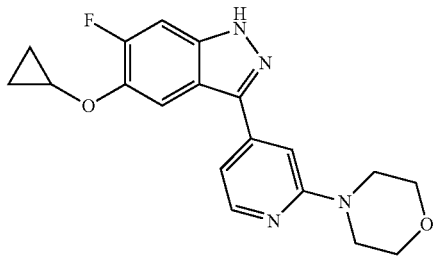 [SMILES: Fc1cc2[nH]nc(-c3ccnc(N4CCOCC4)c3)c2cc1OC1CC1]

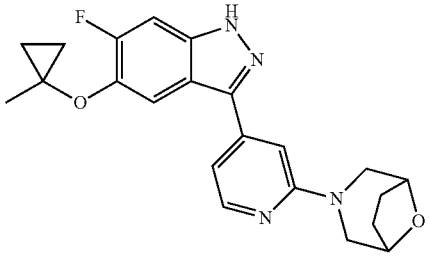 [SMILES: CC1(Oc2ccc3[nH]nc(-c4ccnc(N5CC6CCC(C5)O6)c4)c3c2)CC1]

-continued
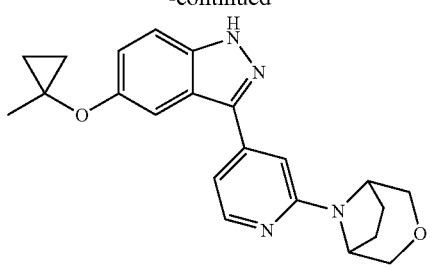
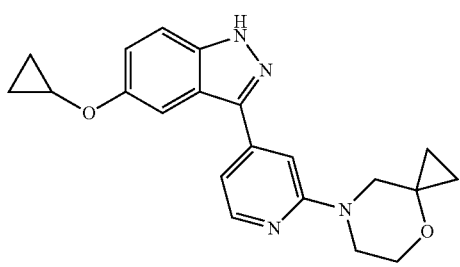 [SMILES: c1cc(-c2n[nH]c3ccc(OC4CC4)cc23)cc(N2CCOC3(CC3)C2)n1]
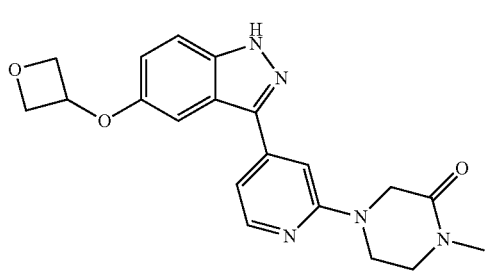 [SMILES: CN1CCN(c2cc(-c3n[nH]c4ccc(OC5COC5)cc34)ccn2)CC1=O]
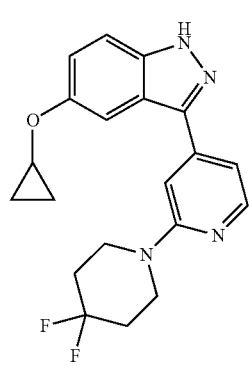 [SMILES: FC1(F)CCN(c2cc(-c3n[nH]c4ccc(OC5CC5)cc34)ccn2)CC1]
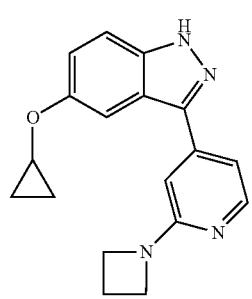 [SMILES: c1cc(-c2n[nH]c3ccc(OC4CC4)cc23)cc(N2CCC2)n1]
-continued
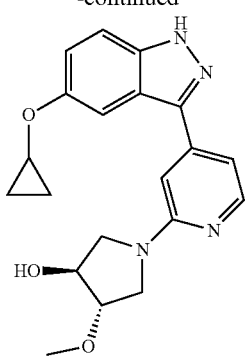
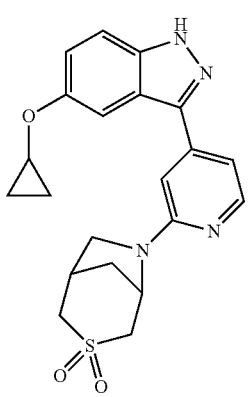 [SMILES: O=S1(=O)CC2CC(C1)N(c1cc(-c3n[nH]c4ccc(OC5CC5)cc34)ccn1)C2]
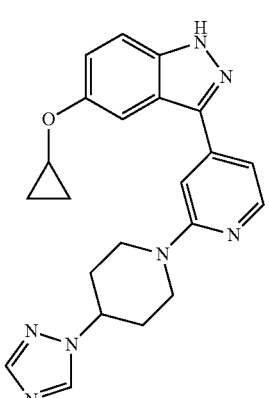
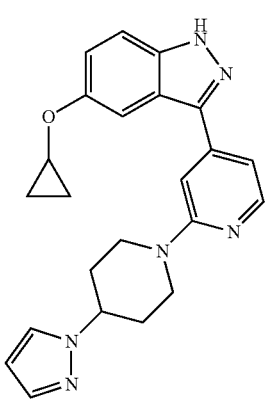 [SMILES: c1cnn(C2CCN(c3cc(-c4n[nH]c5ccc(OC6CC6)cc45)ccn3)CC2)c1]

-continued
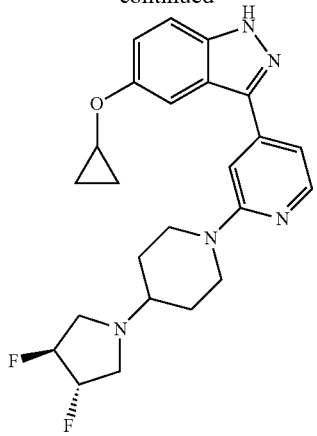
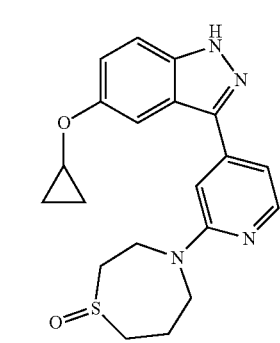
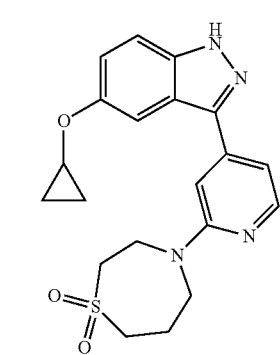
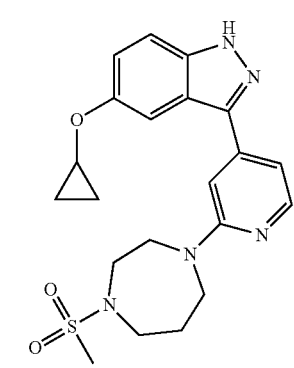
-continued
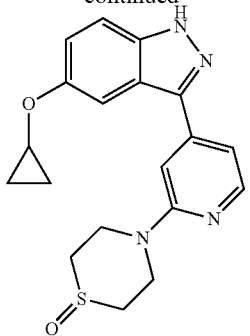
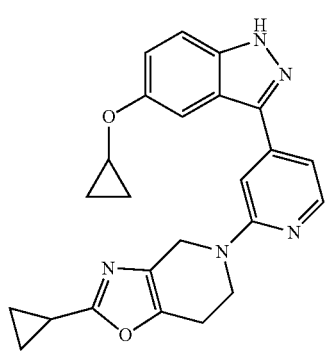
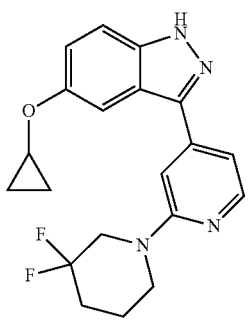 [SMILES: FC1(F)CCCN(c2cc(-c3n[nH]c4ccc(OC5CC5)cc34)ccn2)C1]
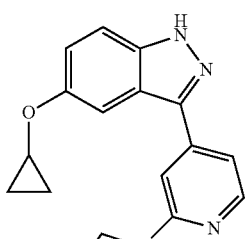
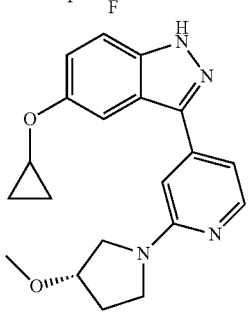

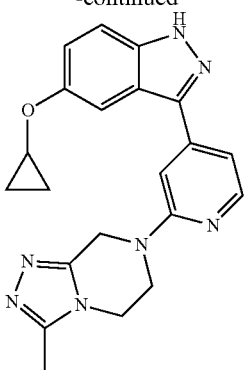
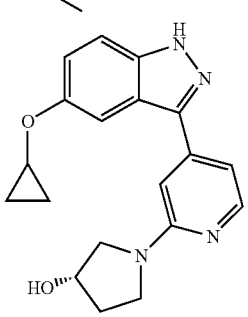
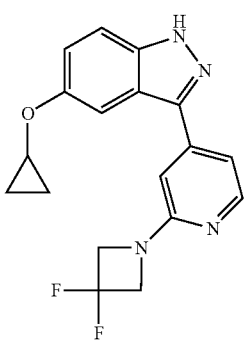 [SMILES: FC1(F)CN(c2cc(-c3n[nH]c4ccc(OC5CC5)cc34)ccn2)C1]
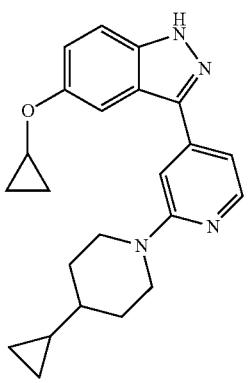 [SMILES: c1cc(-c2n[nH]c3ccc(OC4CC4)cc23)cc(N2CCN(C3CC3)CC2)n1]
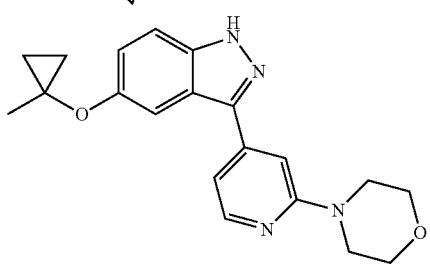
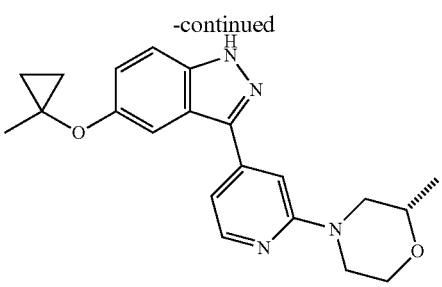
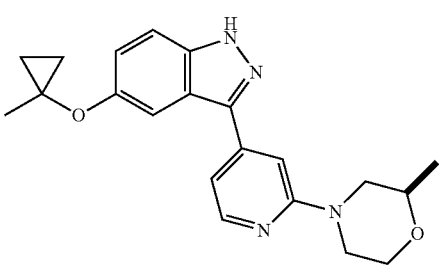
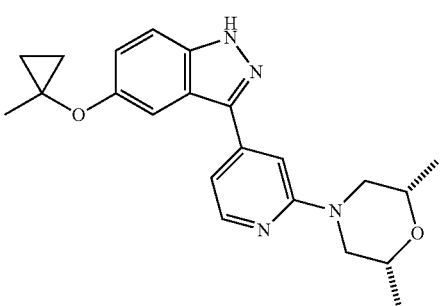
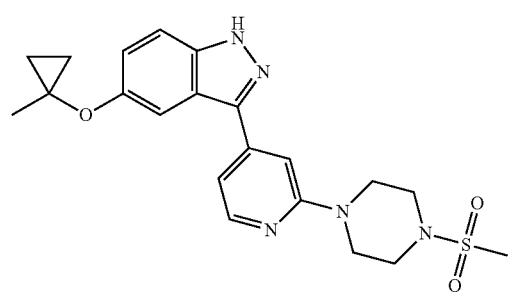
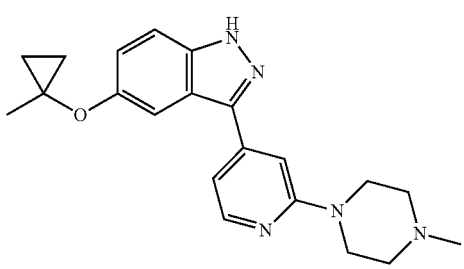

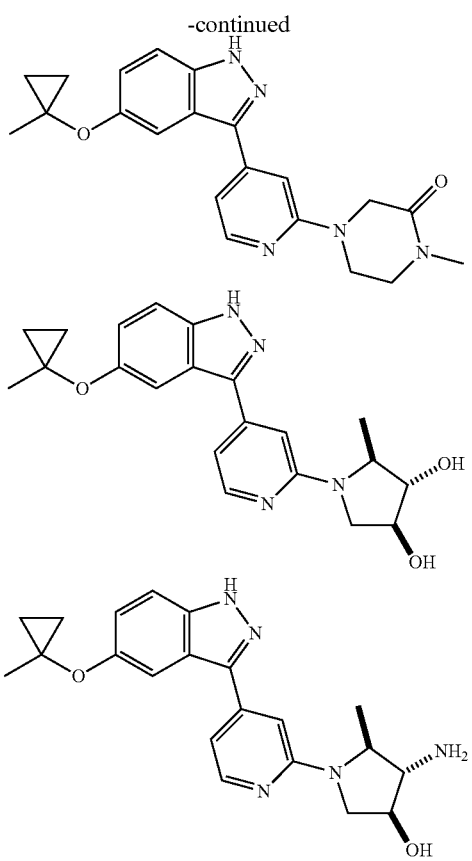
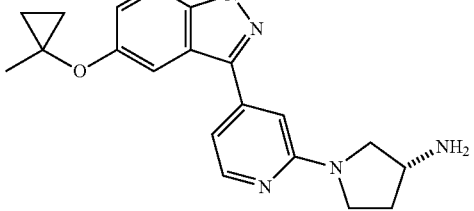
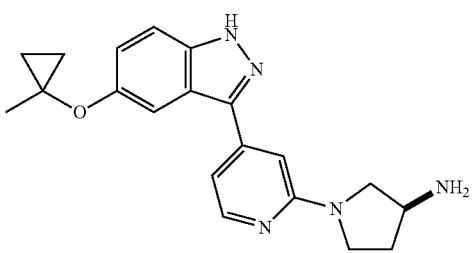 [SMILES: CC1(Oc2ccc3[nH]nc(-c4ccnc(N5CC[C@H](N)C5)c4)c3c2)CC1]
or a pharmaceutically acceptable salt thereof.
9. A pharmaceutical composition comprising a compound of claim 1, and a pharmaceutically acceptable carrier.
10. A method for the treatment of Parkinson's Disease comprising administering a compound of claim 1, or a pharmaceutical composition thereof, to a patient in need thereof.
* * * * *